(12) United States Patent
Kadouri et al.

(10) Patent No.: US 11,185,572 B2
(45) Date of Patent: *Nov. 30, 2021

(54) MESENCHYMAL STEM CELLS FOR THE TREATMENT OF CNS DISEASES

(71) Applicants: Ramot at Tel-Aviv University Ltd., Tel-Aviv (IL); BrainStorm Cell Therapeutics Ltd., Petach-Tikva (IL)

(72) Inventors: Avinoam Kadouri, Petach-Tikva (IL); Avihay Bar-Ilan, Tel-Aviv (IL); Eldad Melamed, Tel-Aviv (IL); Daniel Offen, Tel-Aviv (IL); Ofer Sadan, Tel-Aviv (IL); Merav Bahat-Stromza, Pardes Chana-Karkur (IL)

(73) Assignees: Ramot at Tel-Aviv University Ltd., Tel-Aviv (IL); BrainStorm Ceil Therapeutics Ltd., Petach-Tikva (IL)

( * ) Notice: Subject to any disclaimer, the term of this patent is extended or adjusted under 35 U.S.C. 154(b) by 186 days.

This patent is subject to a terminal disclaimer.

(21) Appl. No.: 16/047,129

(22) Filed: Jul. 27, 2018

(65) Prior Publication Data

US 2018/0333458 A1 Nov. 22, 2018

Related U.S. Application Data

(60) Continuation of application No. 15/261,959, filed on Sep. 11, 2016, now Pat. No. 10,052,363, which is a division of application No. 14/556,281, filed on Dec. 1, 2014, now Pat. No. 9,474,787, which is a division of application No. 14/164,286, filed on Jan. 27, 2014, now Pat. No. 8,900,574, which is a division of application No. 12/994,761, filed as application No. PCT/IL2009/000525 on May 26, 2009, now Pat. No. 8,663,987.

(60) Provisional application No. 61/071,970, filed on May 28, 2008.

(51) Int. Cl.

| | | |
|---|---|---|
| *A61K 38/18* | (2006.01) | |
| *A61K 35/28* | (2015.01) | |
| *C12N 5/0775* | (2010.01) | |
| *C12N 5/079* | (2010.01) | |
| *A61P 25/28* | (2006.01) | |
| *C12N 5/077* | (2010.01) | |
| *A61K 35/12* | (2015.01) | |

(52) U.S. Cl.
CPC ............ *A61K 38/185* (2013.01); *A61K 35/28* (2013.01); *A61P 25/28* (2018.01); *C12N 5/0618* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61K 35/12* (2013.01); *C12N 5/0669* (2013.01); *C12N 2500/84* (2013.01); *C12N 2501/01* (2013.01); *C12N 2501/11* (2013.01); *C12N 2501/115* (2013.01); *C12N 2501/135* (2013.01); *C12N 2506/1346* (2013.01); *C12N 2506/1353* (2013.01)

(58) Field of Classification Search
CPC ...... A61K 38/185; A61K 35/28; A61K 35/12; A61P 25/28; C12N 5/0662; C12N 5/0663; C12N 5/0665; C12N 5/0666; C12N 5/0667; C12N 5/0668; C12N 5/0669; C12N 2506/1346

See application file for complete search history.

(56) References Cited

U.S. PATENT DOCUMENTS

| | | |
|---|---|---|
| 5,229,500 A | 7/1993 | Barde et al. |
| 5,464,764 A | 11/1995 | Capecchi et al. |
| 5,487,992 A | 1/1996 | Capecchi et al. |
| 5,780,587 A | 7/1998 | Potter |
| 5,830,621 A | 11/1998 | Suzuki et al. |
| 5,968,829 A | 10/1999 | Carpenter |
| 6,528,245 B2 | 3/2003 | Sanchez-Ramos et al. |
| 6,576,464 B2 | 6/2003 | Gold et al. |
| 6,673,606 B1 | 1/2004 | Tennekoon et al. |
| 6,989,271 B2 | 1/2006 | Dezawa et al. |
| 8,647,874 B2 | 2/2014 | Offen et al. |
| 8,663,987 B2 | 3/2014 | Kadouri et al. |
| 8,900,574 B2 | 12/2014 | Kadouri et al. |
| 9,474,787 B2 | 10/2016 | Kadouri et al. |
| 10,052,363 B2 | 8/2018 | Kadouri et al. |
| 2002/0009743 A1 | 1/2002 | Carpenter |
| 2002/0081724 A1 | 6/2002 | Carpenter et al. |
| 2002/0146821 A1 | 10/2002 | Sanchez-Ramos et al. |

(Continued)

FOREIGN PATENT DOCUMENTS

| | | |
|---|---|---|
| AU | 2003207064 | 9/2003 |
| WO | WO 97/32608 | 9/1997 |

(Continued)

OTHER PUBLICATIONS

Autry et al. Brain-Derived Neurotrophic Factor and Neuropsychiatric Disorders. Pharmacol Rev 64:238-258 (Year: 2012).*

(Continued)

*Primary Examiner* — Taeyoon Kim

(57) ABSTRACT

An isolated human cell is disclosed comprising at least one mesenchymal stem cell phenotype and secreting brain-derived neurotrophic factor (BDNF), wherein a basal secretion of the BDNF is at least five times greater than a basal secretion of the BDNF in a mesenchymal stem cell. Methods of generating same and uses of same are also disclosed.

5 Claims, 13 Drawing Sheets
(12 of 13 Drawing Sheet(s) Filed in Color)

(56) References Cited

U.S. PATENT DOCUMENTS

| | | |
|---|---|---|
| 2003/0008273 A1 | 1/2003 | Perlmann et al. |
| 2003/0039639 A1 | 2/2003 | Prockop et al. |
| 2003/0059414 A1 | 3/2003 | Ho et al. |
| 2004/0208858 A1 | 10/2004 | Tennekoon et al. |
| 2005/0265983 A1 | 12/2005 | Melamed et al. |
| 2006/0166362 A1 | 7/2006 | Dezawa et al. |
| 2007/0178591 A1 | 8/2007 | Honmou et al. |
| 2009/0010895 A1 | 1/2009 | Offen et al. |
| 2012/0009673 A1 | 1/2012 | Kadouri et al. |
| 2013/0236964 A1 | 9/2013 | Melamed et al. |
| 2014/0140968 A1 | 5/2014 | Kadouri et al. |
| 2014/0154222 A1 | 6/2014 | Offen et al. |
| 2015/0086517 A1 | 3/2015 | Kadouri et al. |
| 2016/0375098 A1 | 12/2016 | Kadouri et al. |
| 2018/0112185 A1 | 4/2018 | Offen et al. |

FOREIGN PATENT DOCUMENTS

| | | |
|---|---|---|
| WO | WO 99/43286 | 9/1999 |
| WO | WO 99/56759 | 11/1999 |
| WO | WO 01/11011 | 2/2001 |
| WO | WO 01/88104 | 11/2001 |
| WO | WO 02/064748 | 8/2002 |
| WO | WO 02/086108 | 10/2002 |
| WO | WO 03/059272 | 7/2003 |
| WO | WO 2004/046348 | 6/2004 |
| WO | WO 2005/007176 | 1/2005 |
| WO | WO 2006/134602 | 12/2006 |
| WO | WO 2007/066338 | 6/2007 |
| WO | WO 2009/144718 | 12/2009 |

OTHER PUBLICATIONS

Dissociative Disorders. National Allliance on Mental Illness. downloaded from www.nami.org/learn-more/mental-health-conditions/dissociative-disorders on Feb. 14, 2020. p. 1-3 (Year: 2020).*
Tunca et al. Alterations in BDNF (brain derived neurotrophic factor) and GDNF (glial cell line-derived neurotrophic factor) serum levels in bipolar disorder: The role of lithium. JournalofAffectiveDisorders166(2014)193-200 (Year: 2014).*
Mathern et al. Granule cell mRNA levels for BDNF, NGF, and NT-3 correlate with neuron losses or supragranular mossy fiber sprouting in the chronically damaged and epileptic human hippocampus. Molecular and Chemical Neuropathology 30, 53-76. Abstract only. (Year: 1997).*
Tapia-Arancibia et al. Physiology of BDNF: focus on hypothalamic function. Frontiers in Neuroendocrinology 25 (2004) 77-107 (Year: 2004).*
Koyama et al. To BDNF or Not to BDNF: That Is the Epileptic Hippocampus. Neuroscientist 11(4):282-287 (Year: 2005).*
Seifert et al. Astrocyte dysfunction in neurological disorders: a molecular perspective. Nature Reviews. Neuroscience. vol. 7, p. 194-206 (Year: 2006).*
Shoval et al. The possible role of neurotrophins in the pathogenesis and therapy of schizophrenia. European Neuropsychopharmacology 15 (2005) 319-329 (Year: 2005).*
Binder et al. BDNF and epilepsy: too much of a good thing? Trends in Neurosciences vol. 24 No. 1. p. 47-53 (Year: 2001).*
Kanter-Schlife et al. GDNF released from encapsulated cells suppresses seizure activity in the epileptic hippocampus. Experimental Neurology 216 (2009) 413-419 (Year: 2009).*
Virgos et al. Association study of schizophrenia with polymorphisms at six candidate genes. Schizo. Res. 49:65-71 (Year: 2001).*
Official Action dated Dec. 11, 2019 From the US Patent and Trademark Office Re. U.S. Appl. No. 15/820,521. (30 pages).
International Preliminary Report on Patentability dated Jan. 3, 2008 From the International Bureau of WIPO Re. Application No. PCT/IL2006/000699.
International Preliminary Report on Patentability dated Jun. 19, 2008 From the International Bureau of WIPO Re. Application No. PCT/IL2006/001410.
Official Action dated Jun. 11, 2008 From the US Patent and Trademark Office Re. U.S. Appl. No. 11/130,197.
Official Action dated Mar. 13, 2007 From the US Patent and Trademark Office Re. U.S. Appl. No. 11/130,197.
Official Action dated Jan. 27, 2009 From the US Patent and Trademark Office Re. U.S. Appl. No. 11/130,197.
Advisory Action Before the Filing of an Appeal Brief dated Aug. 3, 2017 From the US Patent and Trademark Office Re. U.S. Appl. No. 14/173,846. (3 pages).
Advisory Action Before the Filing of an Appeal Brief dated Apr. 11, 2016 From the US Patent and Trademark Office Re. U.S. Appl. No. 13/783,607.
Advisory Action Before the Filing of an Appeal Brief dated Jul. 24, 2015 From the US Patent and Trademark Office Re. U.S. Appl. No. 14/173,846.
Advisory Action Before the Filing of an Appeal Brief dated May 24, 2017 From the US Patent and Trademark Office Re. U.S. Appl. No. 14/173,846. (3 pages).
Applicant-Initiated Interview Summary dated May 11, 2016 From the US Patent and Trademark Office Re. U.S. Appl. No. 14/556,281.
Applicant-Initiated Interview Summary dated Oct. 15, 2012 From the US Patent and Trademark Office Re. U.S. Appl. No. 11/130,197.
Applicant-Initiated Interview Summary dated Jun. 2017 From the US Patent and Trademark Office Re. U.S. Appl. No. 14/173,846. (4 pages).
Communication Pursuant to Article 94(3) EPC dated Mar. 8, 2007 From the European Patent Office Re. Application No. 03811473.2.
Communication Pursuant to Article 94(3) EPC dated Mar. 4, 2015 From the European Patent Office Re. Application No. 09754337.5.
Communication Pursuant to Article 94(3) EPC dated Feb. 10, 2009 From the European Patent Office Re. Application No. 03811473.2.
Communication Pursuant to Article 94(3) EPC dated Jun. 10, 2010 From the European Patent Office Re. Application No. 06766101.7.
Communication Pursuant to Article 94(3) EPC dated Apr. 2016 From the European Patent Office Re. Application No. 09754337.5.
Communication Pursuant to Article 94(3) EPC dated Apr. 11, 2016 From the European Patent Office Re. Application No. 13164650.7.
Communication Pursuant to Article 94(3) EPC dated Oct. 11, 2017 From the European Patent Office Re. Application No. 13164650.7. (5 Pages).
Communication Pursuant to Article 94(3) EPC dated Nov. 15, 2013 From the European Patent Office Re. Application No. 11000994.1.
Communication Pursuant to Article 94(3) EPC dated Apr. 19, 2011 From the European Patent Office Re. Application No. 09754337.5.
Communication Pursuant to Article 94(3) EPC dated Jun. 25, 2013 From the European Patent Office Re. Application No. 09754337.5.
Communication Pursuant to Article 94(3) EPC dated Nov. 27, 2012 From the European Patent Office Re. Application No. 06766101.7.
Communication Pursuant to Article 96(2) EPC dated Nov. 18, 2005 From the European Patent Office Re. Application No. 03811473.2.
European Search Report and the European Search Opinion dated Dec. 3, 2012 From the European Patent Office Re. Application No. 11000994.1.
European Search Report and the European Search Opinion dated Jun. 28, 2013 From the European Patent Office Re. Application No. 13164650.7.
Examiner-Initiated Interview Summary dated Mar. 14, 2017 From the US Patent and Trademark Office Re. U.S. Appl. No. 14/173,846. (2 pages).
Examiner's Report dated Mar. 6, 2008 From the Australian Government, IP Australia Re. Application No. 2005202128.
Examiner's Report dated Aug. 25, 2010 From the Australian Government, IP Australia Re. Application No. 2007201401.
International Preliminary Report on Patentability dated Dec. 9, 2010 From the International Bureau of WIPO Re. Application No. PCT/IL2009/000525.
International Search Report and the Written Opinion dated Mar. 14, 2007 From the International Searching Authority Re. Application No. PCT/IL2006/001410.
International Search Report and the Written Opinion dated Nov. 23, 2006 From the International Searching Authority Re. Application No. PCT/IL2006/000699.

(56) References Cited

OTHER PUBLICATIONS

International Search Report and the Written Opinion dated Sep. 30, 2009 From the International Searching Authority Re. Application No. PCT/IL2009/000525.
Notice of Allowance dated Apr. 26, 2018 from the US Patent and Trademark Office Re. U.S. Appl. No. 15/261,959. (7 pages).
Office Action dated Oct. 6, 2008 From the Israeli Patent Office Re. Application No. 168647 and Its Translation Into English.
Office Action dated Aug. 14, 2012 From the Israel Patent Office Re. Application No. 209604 and Its Translation Into English.
Official Action dated Dec. 1, 2017 From the US Patent and Trademark Office Re. U.S. Appl. No. 15/261,959. (80 pages).
Official Action dated Oct. 2, 2013 From the US Patent and Trademark Office Re. U.S. Appl. No. 11/727,583.
Official Action dated Dec. 3, 2015 From the US Patent and Trademark Office Re. U.S. Appl. No. 13/783,607.
Official Action dated Dec. 4, 2012 From the US Patent and Trademark Office Re. U.S. Appl. No. 11/130,197.
Official Action dated Jun. 6, 2012 From the US Patent and Trademark Office Re. U.S. Appl. No. 12/085,995.
Official Action dated Aug. 7, 2009 From the US Patent and Trademark Office Re. U.S. Appl. No. 11/130,197.
Official Action dated Dec. 7, 2011 From the US Patent and Trademark Office Re. U.S. Appl. No. 11/130,197.
Official Action dated Sep. 8, 2006 From the US Patent and Trademark Office Re. U.S. Appl. No. 11/130,197.
Official Action dated Nov. 10, 2010 From the US Patent and Trademark Office Re. U.S. Appl. No. 11/727,583.
Official Action dated Mar. 11, 2013 From the US Patent and Trademark Office Re. U.S. Appl. No. 12/994,761.
Official Action dated Apr. 15, 2010 From the US Patent and Trademark Office Re. U.S. Appl. No. 11/130,197.
Official Action dated Jan. 16, 2015 From the US Patent and Trademark Office Re. U.S. Appl. No. 14/173,846.
Official Action dated Mar. 17, 2017 From the US Patent and Trademark Office Re. U.S. Appl. No. 14/173,846. (13 pages).
Official Action dated Apr. 18, 2012 From the US Patent and Trademark Office Re. U.S. Appl. No. 11/130,197.
Official Action dated Mar. 18, 2014 From the US Patent and Trademark Office Re. U.S. Appl. No. 14/164,286.
Official Action dated Feb. 19, 2010 From the US Patent and Trademark Office Re. U.S. Appl. No. 11/727,583.
Official Action dated Jan. 20, 2012 From the US Patent and Trademark Office Re. U.S. Appl. No. 12/085,995.
Official Action dated Aug. 21, 2015 From the US Patent and Trademark Office Re. U.S. Appl. No. 14/173,846.
Official Action dated Aug. 21, 2015 From the US Patent and Trademark Office Re. U.S. Appl. No. 14/556,281.
Official Action dated May 23, 2013 From the US Patent and Trademark Office Re. U.S. Appl. No. 11/727,583.
Official Action dated Jul. 24, 2013 From the US Patent and Trademark Office Re. U.S. Appl. No. 12/994,761.
Official Action dated Mar. 24, 2014 From the US Patent and Trademark Office Re. U.S. Appl. No. 12/085,995.
Official Action dated Jan. 25, 2016 From the US Patent and Trademark Office Re. U.S. Appl. No. 14/556,281.
Official Action dated May 25, 2016 From the US Patent and Trademark Office Re. U.S. Appl. No. 14/173,846.
Official Action dated Apr. 27, 2015 From the US Patent and Trademark Office Re. U.S. Appl. No. 14/173,846.
Official Action dated May 27, 2015 From the US Patent and Trademark Office Re. U.S. Appl. No. 13/783,607.
Official Action dated Nov. 28, 2016 From the US Patent and Trademark Office Re. U.S. Appl. No. 14/173,846. (20 pages).
Official Action dated Jun. 29, 2007 From the US Patent and Trademark Office Re. U.S. Appl. No. 11/130,197.
Official Action dated Oct. 30, 2007 From the US Patent and Trademark Office Re. U.S. Appl. No. 11/130,197.
Restriction Official Action dated Nov. 9, 2011 From the US Patent and Trademark Office Re. U.S. Appl. No. 12/085,995.
Search Report and Written Opinion dated Sep. 22, 2009 From the Intellectual Property Office of Singapore Issued by the Austrian Patent Office Re. Application No. 200718734-7.
Translation of Notice of Reason for Rejection dated Sep. 18, 2009 From the Japanese Patent Office Re. Application No. 2004-553057.
Written Opinion dated Feb. 11, 2006 From the Intellectual Property Office of Singapore Issued by the Australian Patent Office Re. Application No. SG 200503090-3.
Written Opinion dated Oct. 24, 2006 From the Intellectual Property Offfice of Singapore Issued by the Australian Patent Office Re. Applicaiton No. 200503090-3.
Aebischer et al. "Intrathecal Delivery of CNTF Using Encapsulated Genetically Modified Xenogeneic Cells in Amyotrophic Lateral Sclerosis Patients", Nature Medicine, 2(6): 696-699, Jun. 1996.
Aldous et al. "Fresh Questions on Stem Cell Findings", New Scientist Magazine, 2596: 12-13, 2007.
Bahat-Stroomza et al. "Induction of Adult Human Bone Marrow Mesenchymal Stromal Cells Into Functional Astrocyte-Like Cells: Potential for Restorative Treatment in Parkinson's Disease", Journal of Molecular Neuroscience, XP009164575, 39(1-2): 199-210, Sep. 2009.
Bendotti et al. "Transgenic SOD1 G93A Mice Develop Reduced GLT-1 in Spinal Cord Without Alterations in Cerebrospinal Fluid Glutamate Levels", Journal of Neurochemistry, 79: 737-746, 2001.
Bernardo et al. "Optimization of In Vitro Expansion of Human Multipotent Mesenchymal Stromal Cells for Cell-Therapy Approaches: Further Insights in the Search for a Fetal Calf Serum Substitute", Journal of Cellular Physiology, XP002545729, 211(1): 121-130, Apr. 2007.
Black et al. "Adult Rat and Human Bone Marrow Stromal Stem Cells Differentiate Into Neurons", Blood Cells, Molecules, and Diseases, 27(3): 632-636, 2001.
Blondheim et al. "Human Mesenchymal Stem Cells Express Neural Genes, Suggesting a Neural Predisposition", Stem Cells and Development, XP009079870, 15(2): 141-164, Apr. 2006.
Boado et al. "Comparison of Blood-Brain Barrier Transport of Glial-Derived Neurotrophic Factor (GDNF) and an IgG-GDDNF Fusion Protein in the Rhesus Monkey", Drug Metabolism and Disposition, 37(12): 2299-2304, 2009.
Bossolasco et al. "Neuro-Glial Differentiation of Human Bone Marrow Stem Cells In Vitro", Experimental Neurology, XP004875161, 193(2): 312-325, Feb. 17, 2005. Abstract, p. 313, Left col. 'Materials and Methods'—p. 320, Left col., 2nd §, All Figs., p. 320, r-h col., Lines 4-8, Fig.6, Table 1a, p. 321, r-h col., Paragraph 3, p. 319-320.
Bourre et al. "Effect of Polyunsaturated Fatty Acids on Fetal Mouse Brain Cells in Culture in a Chemically Defined Medium", Journal of Neurochemistry, 41: 1234-1242, 1983.
Brierley et al. "Remyelination of Demyelinated CNS Axons by Transplanted Human Schwann Cells: the Deleterious Effect of Contaminating Fibroblasts", Cell Transplant, 10(3): 305-315, 2001. Abstract.
Bruestle et al. "Embryonic Stem Cell-Derived Glial Precursors: A Source of Myelinating Transplants", Science, 285(5428): 754-756, Jul. 30, 1999.
Burchill et al. "Neuroblastoma Cell Detection by Reverse Transcriptase-Polymerase Chain Reaction (RT-PCR) for Tyrosine Hydroxylase mRNA", International Journal of Cancer, 57: 671-675, 1994.
Burdge et al. "Effect of Fatty Acid Supplementation on Growth and Differentiation of Human IMR-32 Neuroblastoma Cells In Vitro", Journal of Cellular Biochemistry, 80: 266-273, 2000.
Canaple et al. "Improving Cell Encapsulation Through Size Control", Journal of Biomaterials Science, Polymer Edition, 13(7): 783-796, 2002.
Capelli et al. "Human Platelet Lysate Allows Expansion and Clinical Grade Production of Mesenchymal Stromal Cells From Small Samples of Bone Marrow Aspirates or Marrow Filter Washouts", Bone Marrow Transplantation, XP002545732, 40(8): 785-791, Oct. 2007.
Carozzi et al. "Expression and Distribution of 'High Affinity' Glutamate Transporter GLT1, GLAST, EAAC1 and of GCPII in the Rat Peripheral Nervous System", Journal of anatomy, 213: 539-546, 2008.

(56) References Cited

OTHER PUBLICATIONS

Chang et al. "Procedures for Microencapsulation of Enzymes, Cells and Genetically Engineered Microorganisms", Molecular Biotechnology, 17: 249-260, 2001.
Check "The Hard Copy", Nature, 446: 485-486, 2007.
Chia et al. "Multi-Layered Microcapsules for Cell Encapsulation", Biomaterials, 23: 849-856, 2002.
Chu et al. "Signalling Pathway in the Induction of Neurite Outgrowth in Human Mesenchymal Stem Cells", Cellular Signalling, 18: 519-530, 2006.
Crigler et al. "Human Mesenchymal Stem Cell Subpopulations Express a Variety of Neuro-Regulatory Molecules and Promote Neuronal Cell Survival and Neuritogenesis", Experimental Neurology, 198: 54-64, 2006.
De Hemptinne et al. "Induction of Glial Glutamate Transporters in Adult Mesenchymal Stem Cells", Journal of Neurochemistry, 91(1): 155-166, Oct. 2004. Abstract, p. 156, Right col. 'Materials and Methods'—p. 162, Right col., First §, All Figs.
Deng et al. "In Vitro Differentiation of Human Marrow Stromal Cells Into Early Progenitors of Neural Calls by Conditions That Increase Intracellular Cyclic AMP", Biochemical and Biophysical Research Communications, 282: 148-152, 2001.
Deng et al. "Mesenchymal Stem Cells Spontaneously Express Neural Proteins in Culture and Are Neurogenic After Transplantation", Stem Cells, XP009164563, 24(4): 1054-1064, Apr. 1, 2006. p. 1057-1058.
Desai "Microfabrication Technology for Pancreatic Cell Encapsulation", Expert Opinion on Biological Therapy, 2(6): 633-646, 2002.
Dezawa et al. "Sciatic Nerve Regeneration in Rats Induced by Transplantation of In Vitro Differentiated Bone-Marrow Stromal Cells", European Journal of Neuroscience, XP002957136, 14(11): 1771-1776, Dec. 1, 2001. p. 1774.
Dormady et al. "Immortalized Multipotential Mesenchymal Cells and the Hematopoietic Microenvironment", Journal of Hematotherapy & Stem Cell Research, XP009074458, 10(1): 125-140, Feb. 2001. p. 125, p. 134-138.
Doucet et al. "Platelet Lysates Promote Mesenchymal Stem Cell Expansion: A Safety Substitute for Animal Serum in Cell-Based Therapy Applications", Journal of Cellular Physiology, XP002545728, 205(2): 228-236, Nov. 2005.
Farlie et al. "Bcl-2 Transgene Expression Can Protect Neurons Against Developmental and Induced Cell Death", Proc. Natl. Acad. Sci. USA, 92: 4397-4401, May 1995.
Garcia et al. "Bone Marrow Stromal Cells Produce Nerve Growth Factor and Glial Cell Line-Derived Neurotrophic Factors", Biochemical and Biophysical Research Communications, XP004495951, 316(3): 753-754, Apr. 9, 2004.
Giess et al. "Early Onset of Severe Familial Amyotrophic Lateral Sclerosis With a SOD-1 Mutation: Potential Impact of CNTF as a Candidate Modifier Gene", American Journal of Human Genetics, 70: 1277-1286, 2002.
Giraldo "Overview of Stroke", Merck Manuals, 7 Pages, Nov. 2013.
Gonzalez-Usigli "Huntington Disease", Merck Manuals, 4 Pages, Sep. 2015.
Gonzalez-Usigli "Parkinson Disease", Merck Manuals, 14 Pages, Sep. 2015.
Goodwin et al. "Multilineage Differentiation Activity by Cells Isolated From Umbilical Cord Blood: Expression of Bone, Fat, and Neural Markers", Biology of Blood and Marrow Transplantation, 7: 581-588, 2001.
Henriques et al. "Neurotrophic Growth Factors for the Treatment of Amyotrophic Lateral Sclerosis: Where Do We Stand?", Frontiers in Neuroscience, 4(Art.32): 1-14, Jun. 2010.
Ikemoto et al. "Membrane Fatty Acid Modifications of PC12 Cells by Arachidonate or Docosahexaenoate Affect Neurite Outgrowth But Not Norephinephrine Release", Neurochemical Research, 22(6): 671-678, 1997.
Jiang et al. "Pulripotency of Mesenchymal Stem Cells Derived From Adult Marrow", Nature, 418: 41-49, 2002.
Jones et al. "Human Neutrotrophin-3 (NT-3) Gene, Complete CDS", Database NCBI [Online], GenBank: M37763.1, GenBank Accession No. M37763, Jan. 7, 1995.
Kafri et al. "Lentiviral Vectors: Regulated Gene Expression", Molecular Therapy, 1(6): 516-521, 2000.
Kaisho et al. "Nerve Growth Factor [*Homo sapiens*]", NGF Database [Online], GenBank: CAA37703.1, GenBank Accession No. CAA37703, Mar. 11, 1993.
Kan et al. "Docosahexaenoic Acid and Arachidonic Acid Are Fundamental Supplements for Induction of Neuronal Differentiation", Journal of Lipid Research, 55: 1-18, 2007.
Kan et al. "Integral Therapeutic Potential of Bone Marrow Mesenchymal Stem Cells", Current Drug Targets, 6: 31-41, 2005.
Kandel et al. "Principles of Neural Science", 3rd Edition (26): 367-384, 1993.
Kassis et al. "Isolation of Mesenchymal Stem Cells From G-CSF-Mobilized Human Peripheral Blood Using Fibrin Microbeads", Bone Marrow Transplantation, 37: 967-976, 2006.
Keilhoff et al. "Transdifferentiation of Mesenchymal Stem Cells Into Schwann Cell-Like Myelinating Cells", European Journal of Cell Biology, 85: 11-24, 2006.
Kern et al. "Comparative Analysis of Mesenchymal Stem Cells From Bone Marrow, Umbilical Cord Blood, or Adipose Tissue", Stem Cells, 24: 1294-1301, 2006.
Kirsch et al. "Characterization and Intracellular Distribution of Microtubule-Associated Protein 2 in Differentiating Human Neuroblastoma Cells", Journal of Neurochemistry, 55: 1031-1041, 1990.
Kohama et al. "Transplantation of Cryopreserved Adult Human Schwann Cells Enhances Axonal Conduction in Demyelinated Spinal Cord", Journal of Neuroscience, 21(3): 944-950, Feb. 2001.
Kohyama et al. "Brain From Bone: Efficient 'Meta-Differentiation' of Marrow Stroma-Derived Mature Osteoblasts to Neurons With Noggin or a Demethylating Agent", Differentiation, 68: 235-244, 2001.
Kopen et al. "Marrow Stromal Cells Migrate Throughout Forebrain and Cerebellum, and They Differentiate Into Astrocytes After Injection Into Neonatal Mouse Brains", Proc. Natl. Acad. Sci. USA, 96: 10711-10716, 1999.
Kramer et al. "Adult Rat Bone Marrow Stromal Cells Express Genes Associated With Dopamine Neurons", Biochemical and Biophysical Research Communications, XP024924814, 343(4): 1045-1052, May 19, 2006.
Kurozumi et al. "BDNF Gene-Modified Mesenchymal Stem Cells Promote Functional Recovery and Reduce Infarct Size in the Rat Middle Cerebral Artery Occlusion Model", Molecular Therapy, 9(2): 189-197, Feb. 2004.
Kurozumi et al. "Mesenchymal Stem Cells That Produce Neurotrophic Factors Reduce Ischemic Damage in the Rat Middle Cerebral Artery Occlusion Model", Molecular Therapy, XP004672531, 11(1): 96-104, Jan. 1, 2005.
Lange et al. "Accelerated and Safe Expansion of Human Mesenchymal Stromal Cells in Animal Serum-Free Medium for Transplantation and Regenerative Medicine", Journal of Cellular Physiology, XP002545733, 213(1): 18-26, Oct. 2007.
Lee et al. "Migration and Differentiation of Nuclear Fluorescence-Labeled Bone Marrow Stromal Cells After Transplantation Into Cerebral Infarct and Spinal Cord Injury in Mice", Neuropathology, 23(3): 169-180, Sep. 2003. Abstract.
Levy et al. "Embryonic and Adult Stem Cells as a Source for Cell Therapy in Parkinson's Disease", Journal of Molecular Neuroscience, 24: 353-385, 2004.
Levy et al. "Induction of Neuron-Specific Enolase Promoter and Neuronal Markers in Differentiated Mouse Bone Marrow Stromal Cells", Journal of Molecular Neuroscience, 21: 121-132, 2003.
Li et al. "Intracerebral Transplantation of Bone Marrow Stromal Cells in a 1-Methyl-4-Phenyl-,-1,2,3,6-Tetrahydropyridine Mouse Model of Parkinson's Disease", Neuroscience Letters, 316(2): 67-70, 2001.
Li et al. "Intrastriatal Transplantation of Bone Marrow Nonhematopoietic Cells Improves Functional Recovery After Stroke in Adult Mice", Journal of Cerebral Blood Flow and Metabolism, 20: 1311-1319, 2000.

(56) References Cited

OTHER PUBLICATIONS

Life Technologies "Technical Resources—Media Formulations. N-2 Supplement (100X) Liquid", Life Technologies Corporation, 1 P., 2013.
Lu et al. "A Novel Cell Encapsulation Method Using Photosensitive Poly(Allylamine Alpha-Cyanocinnam Ylideneacytate)", Journal of Microencapsulation, 17(2): 245-251, 2000.
Lu et al. "Cell Encapsulation With Alginate and ?-Phenoxycinnamylidene-Acetylated Poly(Allylamine)", Biotechnology and Bioengineering, 70: 479-483, 2000.
Lu et al. "Induction of Bone Marrow Stromal Cells to Neurons: Differentiation, Transdifferentiation, or Artifact?", Journal of Neuroscience Research, 77: 174-191, 2004.
Magaki et al. "Generation of Bone Marrow-Derived Neural Cells in Serum-Free Monolayer Culture", Neuroscience Letters, 384: 282-287, 2005.
Mahmood et al. "Treatment of Traumatic Brain Injury in Female Rats With Intravenous Administration of Bone Marrow Stromal Cells", Neurosurgery, 49: 1196-1204, 2001.
Mehta et al "Enhancement of Graft Survival and Sensorimotor Behavioral Recovery in Rats Undergoing YTransplantation with Dopaminergic Cells Exposed to Glial Cell Line-Derived Neurotrophic Factor", Journal of Neurosurg, 88(6):1088-1095, Jun. 1998.
Mehta et al. "Graft Survival", Journal of Neurosurgery, 90: 804-806, 1999.
Mohajeri et al. "Intramuscular Grafts of Myoblasts Genetically Modified to Secrete Glial Cell Line-Derived Neurotrophic Factor Prevent Motoneuron Loss and Disease Progression in a Mouse Model of Familial Amyotrophic Lateral Sclerosis", Human Gene Therapy, 10: 1853-1866, Jul. 20, 1999.
Moore "Polyunsaturated Fatty Acid Synthesis and Release by Brain-Derived Cells In Vitro", Journal of Molecular Neuroscience, 16: 195-200, 2001.
Moore et al. "Astrocytes, Not Neurons, Produce Docosahexaenoic Acid (22:6Omega-3) and Arachidonic Acid (20:4Omega-6)", Journal of Neurochemistry, 56: 518-524, 1991.
Munoz et al. "Human Adult Stem Cells From Bone Marrow Stroma Express Trophic Factors in Culture and Following Transplantation in Brain", Society for Neuroscience, Abstract Viewer and Itinerary Planner, XP002405240, 2003: Abstract No. 300.16, 2003. Abstract. & 33rd Annual Meeting of the Society of Neuroscience, New Orleans, LA, USA, Nov. 8-12, 2003.
Musina et al. "Comparison of Mesenchymal Stem Cells Obtained From Different Human Tissues", Cell Technologies in Biology and Medicine, 1(2): 504-509, Apr. 2005.
Ohishi et al. "GDNF Expression in Terminal Schwann Cells Associated With the Periodontal Ruffini Endings of the Rat Incisors During Nerve Regeneration", Anatomical Record, 292(8): 1185-1191, Aug. 2009. Abstract.
Padovan et al. "Expression of Neuronal Markers in Differentiated Marrow Stromal Cells and CD133+ Stem-Like Cells", Cell Transplantation, XP009117445, 12(8) 839-848, Jan. 1, 2003. p. 842-843.
Park et al. "Protection of Nigral Neurons by GDNF-Engineered Marrow Cell Transplantation", Neuroscience Research, 40: 315-323, 2001.
Raff "Glial Cell Diversification in the Rat Optic Nerve", Science, 243(4897): 1450-1455, Mar. 1989. Abstract.
Reinisch et al. "Humanized System to Propagate Cord Blood-Derived Multipotent Mesenchymal Stromal Cells for Clinical Application", Regenerative Medicine, XP002545730, 2(4): 371-382, Jul. 2007.
Rendahl et al. "Regulation of Gene Expression In Vivo Following Transduction by Two Separate Raav Vectors", Nature Biotechnology, 16: 757-761, 1998.
Reyes "Turning Marrow Into Brain: Generation of Glial and Neuronal Cells From Adult Bone Marrow Mesenchymal Stem Cells", Blood, 94(10): 377A, 1999. Abstract. Abstract.
Reyes et al. "Characterization of Multipotent Adult Progenitor Cells, A Subpopulation of Mesenchymal Stem Cells", Annals of the New York Academy of Sciences, 938: 231-235, 2001.

Reynolds et al. "A Multipotent EGF-Responsive Striatal Embryonic Progenitor Cell Produces Neurons and Astrocytes", The Journal of Neuroscience, 12(11): 4565-4574, 1992.
Reynolds et al. "Generation of Neurons and Astrocytes From Isolated Cells of the Adult Mammalian Central Nervous System", Science, 255: 1707-1710, 1992.
Rubin "Amyotrophic Lateral Sclerosis (ALS) and Other Motor Neuron Diseases (MNDs)", Merck Manuals, 7 Pages, Sep. 2016.
Sadan et al. "Adult Neurotrophic Factor-Secreting Stem Cells: A Potential Nocel Therapy for Neurodegenerative Diseases", The Israeli Medical Association Journal, XP002545735, 11(4): 201-204, Apr. 2009.
Sadan et al. "Migration of Neurotrophic Factors-Secreting Mesenchymal Stem Cells Toward a Quinolinic Acid Lesion as Viewed by Magnetic Resonance Imaging", Stem Cells, XP002545734, 26(10): 2542-2551, Oct. 2008.
Saitoh et al. "Proteasomal Degradation of Glutamine Synthetase Regulates Schwann Cell Differentiation", Journal of Neuroscience, 30(4): 1204-1212, Jan. 27, 2010. Abstract.
Sakane et al. "Carboxyl-Directed Pegylation of Brain-Derived Neurotrophic Factor Markedly Reduces Systemic Clearance With Minimal Loss of Biologic Activity", Pharmaceutical Research, 14(8): 1085-1091, Aug. 1997.
Sambanis "Encapsulated Islets in Diabetes Treatment", Diabetes Technology & Therapeutics, 5(4): 665-668, 2003.
Sanchez-Ramos et al. "Adult Bone Marrow Stromal Cells Differentiate Into Neural Cells In Vitro", Experimental Neurology, 164: 247-256, 2000.
Sasaki et al. "Transplantation of an Acutely Isolated Bone Marrow Fraction Repairs Demyelinated Adult Rat Spinal Cord Axons", GLIA, 35: 26-34, 2001.
Schallmoser et al. "Human Platelet Lysate Can Replace Fetal Bovine Serum for Clinical-Scale Expansions of Functional Mesenchymal Stromal Cells", Transfusion, XP002545731, 47(8): 1436-1446, Aug. 2007.
Schuldiner et al. "Effects of Eight Growth Factors on the Differentiation of Cells Derived From Human Embryonic Stem Cells", Proc. Natl. Acad. Sci. USA, PNAS, 97(21): 11307-11312, Oct. 10, 2000.
Schwarz et al. "Multipotential Marrow Stromal Cells Transduced to Produce L-DOPA: Engraftment in a Rat Model of Parkinson Disease", Human Gene Therapy, 10(15): 2539-2549, 1999. p. 2542-2544, p. 2546-2548.
Schwarz et al. "Rat Marrow Stromal Cells Rapidly Transduced With a Self-Inactivating Retrovirus Synthesize L-DOPA In Vitro", Gene Therapy, 8(16); 1214-1223, 2001. p. 1215, p. 1218, p. 1219-1220.
Spiegel "Overview of Dissociative Disorders" Merck Manuals, 2 Pages, Jul. 2015.
Stenevi et al. "Transplantation of Central and Peripheral Monoamine Neurons to the Adult Rat Brain: Techniques and Conditions for Survival", Brain Research, 114: 1-20, 1976.
Stoll et al. "Changes in Serum Influence the Fatty Acid Composition of Established Cell Lines", In Vitro, 20: 732-738, Sep. 9, 1984.
Suzuki et al. "Neurospheres Induced From Bone Marrow Stromal Cells Are Multipotent for Differentiation Into Neuron, Astrocyte, and Oligodendrocyte Phenotypes", Biochemical and Biophysical Research Communications, 322(3): 918-922, Sep. 2004. Abstract.
Tohill et al. "Rat Bone Marrow Mesenchymal Stem Cells Express Glial Markers and Stimulate Nerve Regeneration", Neuroscience Letters, XP009164562, 362(3): 200-203, May 27, 2004. p. 201.
Tondreau et al. "Bone Marrow-Derived Mesenchymal Stem Cells Already Express Specific Neural Proteins Before Any Differentiation", Differentiation, XP026770125, 72(7): 319-326, Sep. 1, 2004. Abstract, p. 320, r-h col., Paragraph 3, p. 320, Left col., 2nd §—p. 324, Right col., First §, All Figs.
Uludag et al. "Technology of Mammalian Cell Encapsulation", Advanced Drug Delivery Reviews, 42: 29-64, 2000.
Wagner et al. "Mesenchymal Stem Cell Preparations—Comparing Apples and Oranges", Stem Cell Reviews, XP002545736, 3(4): 239-248, Dec. 2007.
Williams "Small Is Beautiful: Microparticle and Nanoparticle Technology in Medical Devices", Medical Device Technology, 10: 6-9, 1999.

(56) References Cited

OTHER PUBLICATIONS

Winkler et al. "Short-Term GDNF Treatment Provides Long-Term Rescue of Lesioned Nigral Dopaminergic Neurons in a Rat Model of Parkinson's Disease", The Journal of Neuroscience, 16(22): 7206-7215, Nov. 15, 1996.

Wislet-Gendebien et al. Astrocytic and Neuronal Fate of Mesenchymal Stem Cells Expressing Nestin, Brain Research Bulletin, 68: 95-102, 2005.

Woodbury et al. "Adult Bone Marrow Stromal Stem Cells Express Germline, Ectodermal, Endodermal, and Mesodermal Genes Prior to Neurogenesis", Journal of Neuroscience Research, 96: 908-917, 2002.

Woodbury et al. "Adult Rat and Human Bone Marrow Stromal Cells Differentiate Into Neurons", Journal of Neuroscience Research, 61: 364-370, 2000.

Yarowsky et al. "Development of Saxitoxin-Sensitive and Insensitive Sodium Channels in Cultured Neonatal Rat Astrocytes", The Journal of Neuroscience, 9(3): 1055-1061, Mar. 1989.

Ye et al. "Glial Cell Line-Derived Neurotrophic Factor in Bone Marrow Stromal Cells of Rat", NeuroReport, 16(6): 581-584, Apr. 25, 2005.

Zhang et al. "Comparison of Mesenchymal Stem Cells from Human Placenta and Bone Marrow", Chinese Medical Journal, 117(6): 882-887, 2004.

Final Official Action dated Apr. 24, 2020 from the US Patent and Trademark Office Re. U.S. Appl. No. 15/820,521. (11 pages).

Advisory Action dated Sep. 8, 2020 from the US Patent and Trademark Office Re. U.S. Appl. No. 15/820,521. (8 pages).

\* cited by examiner

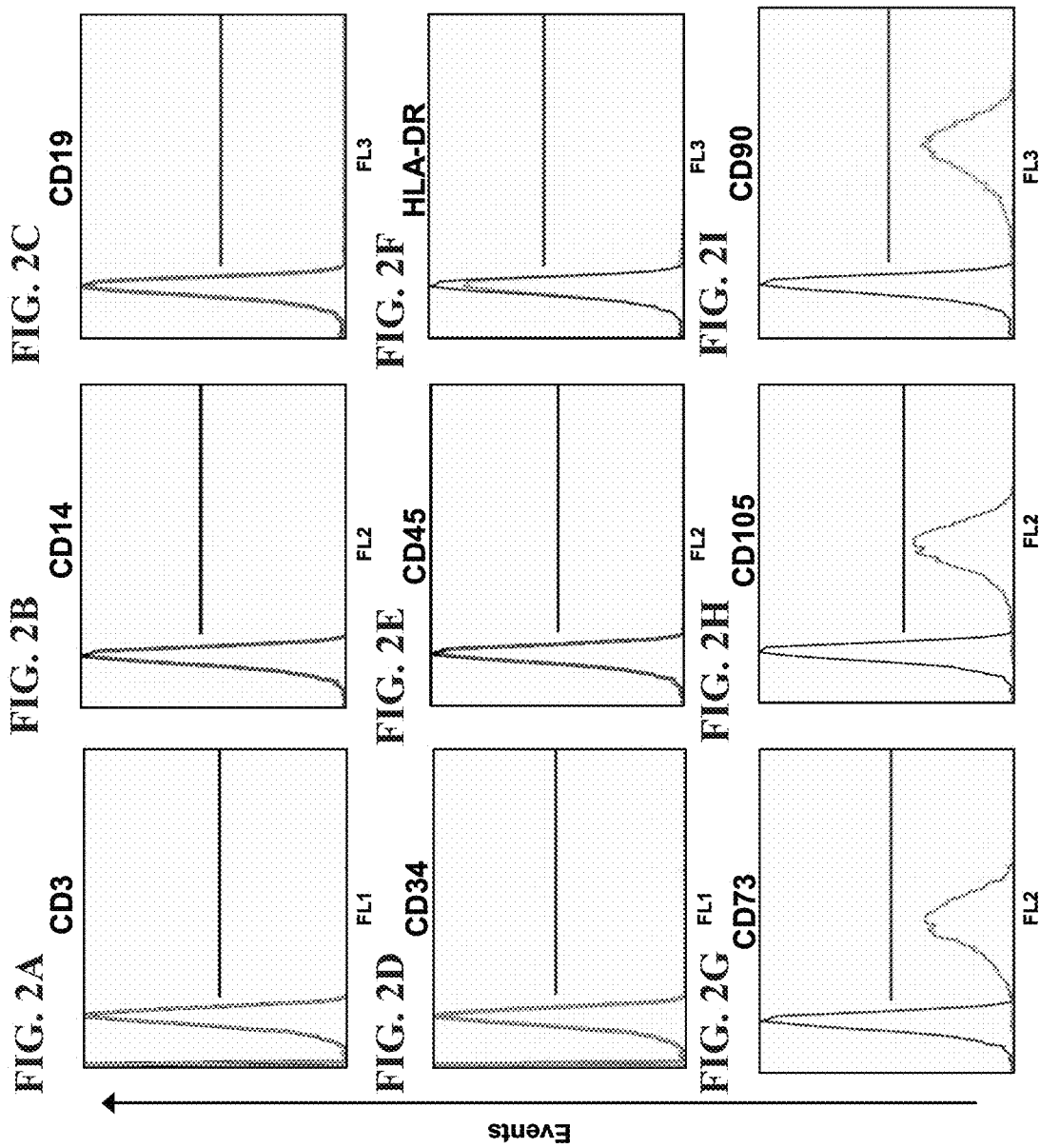

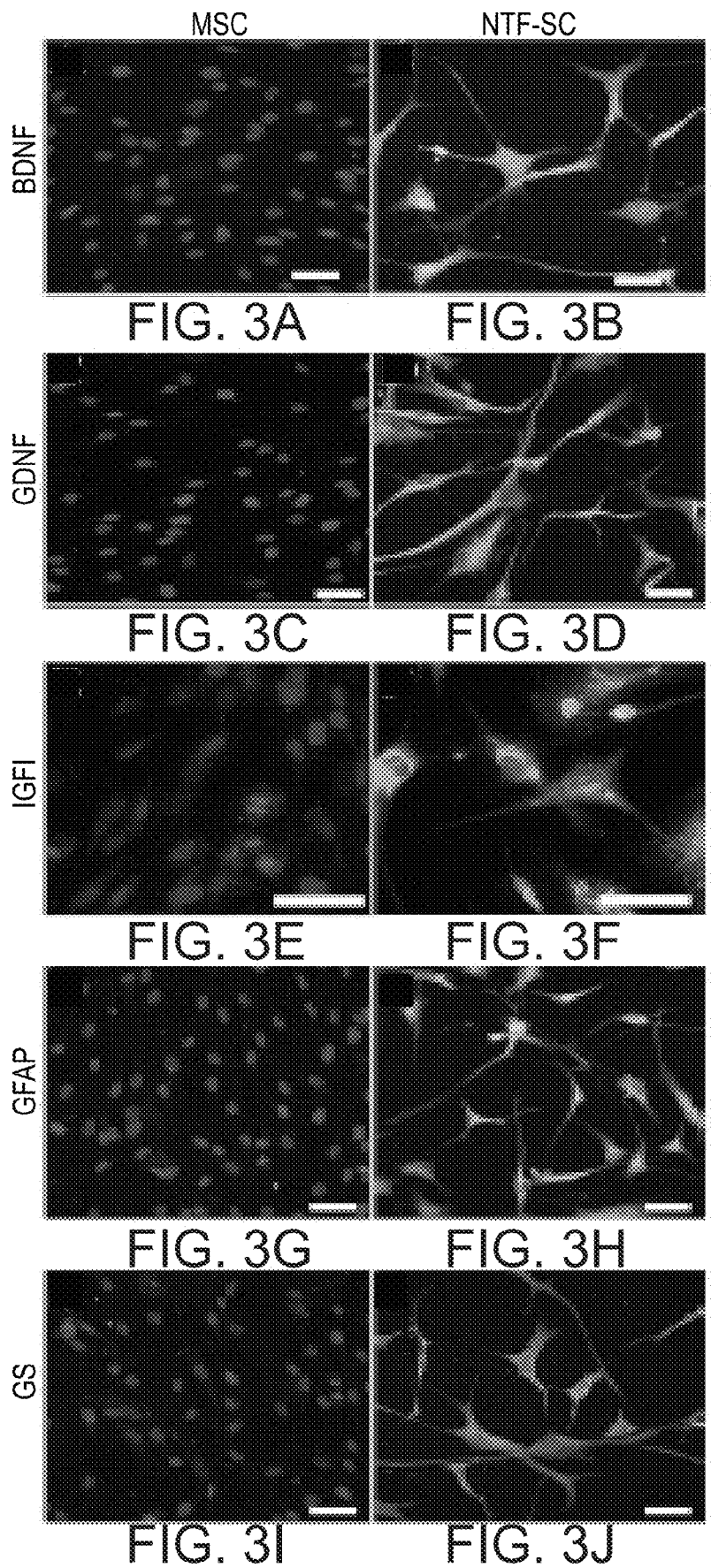

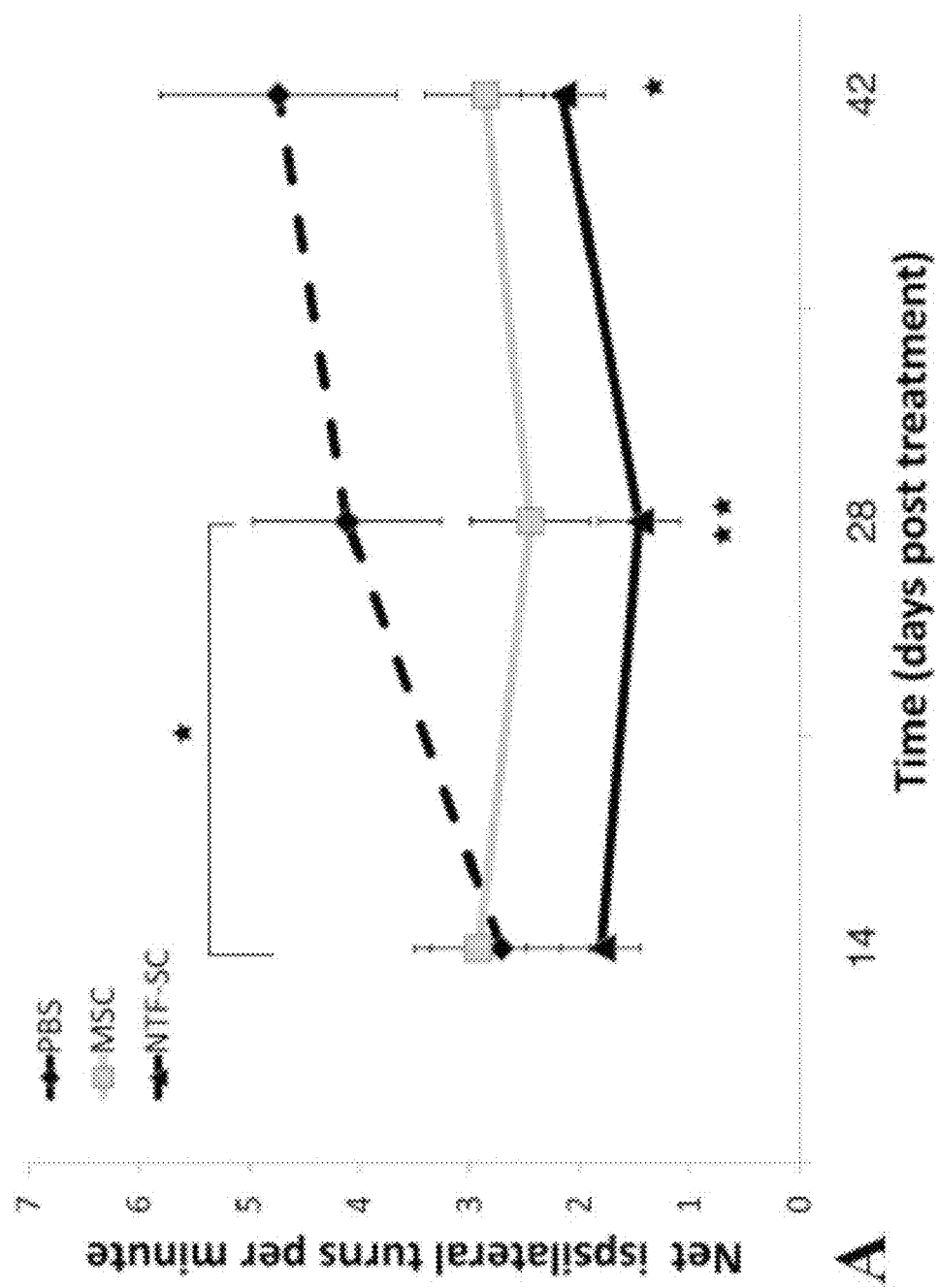

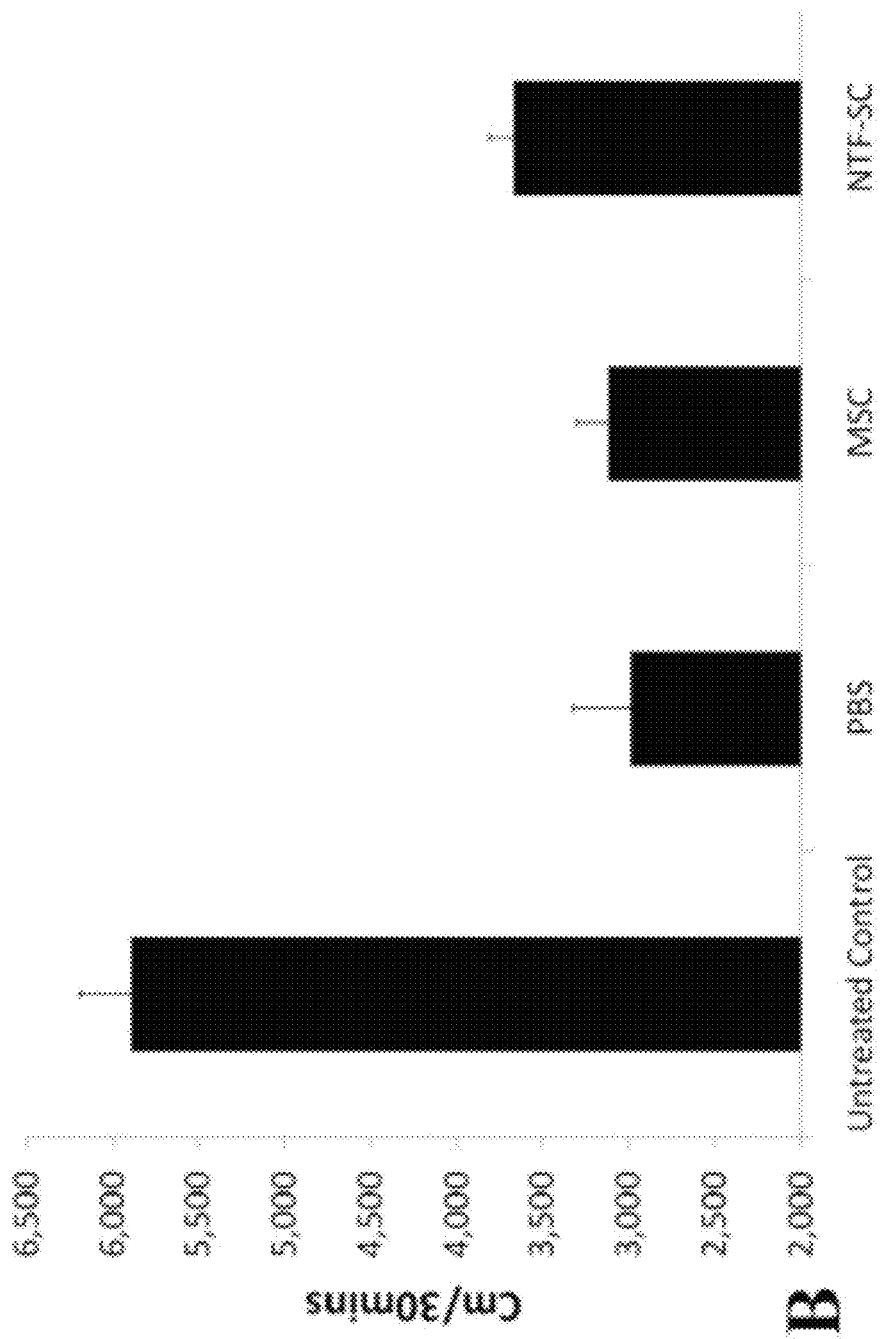

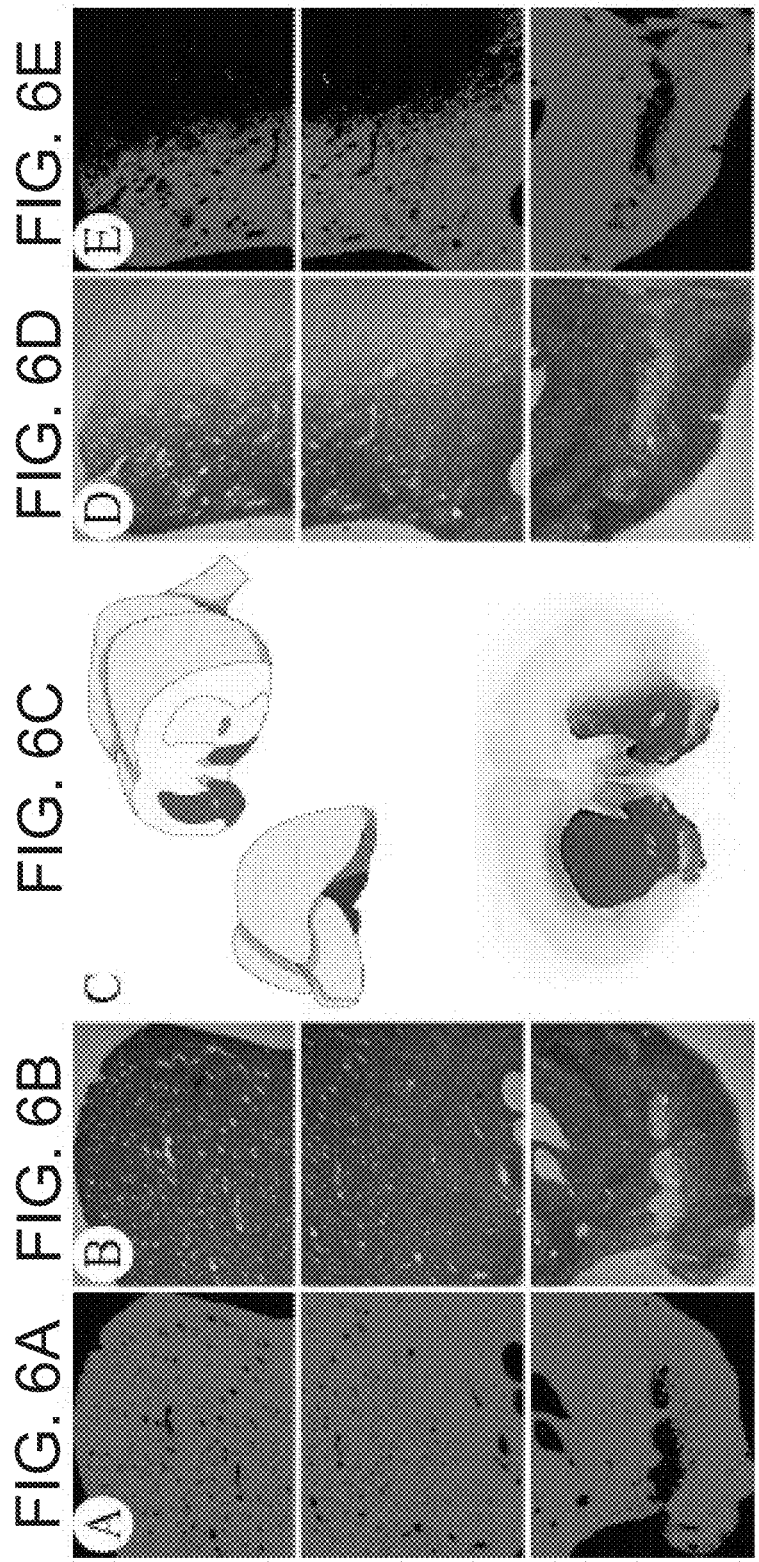

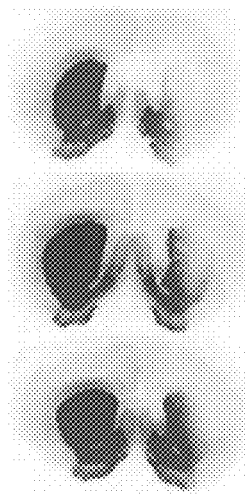
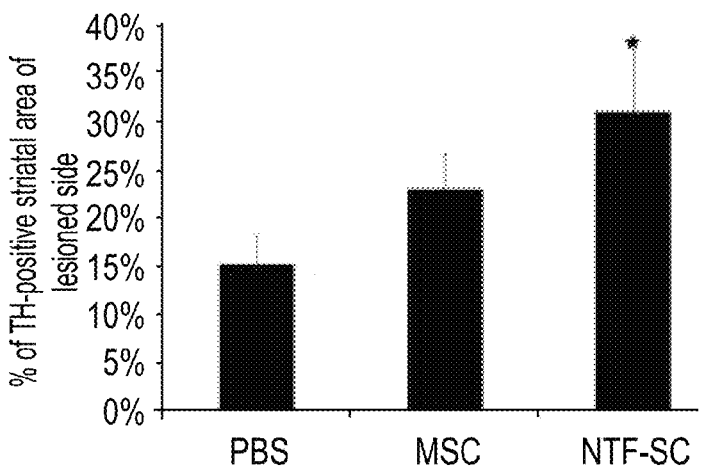
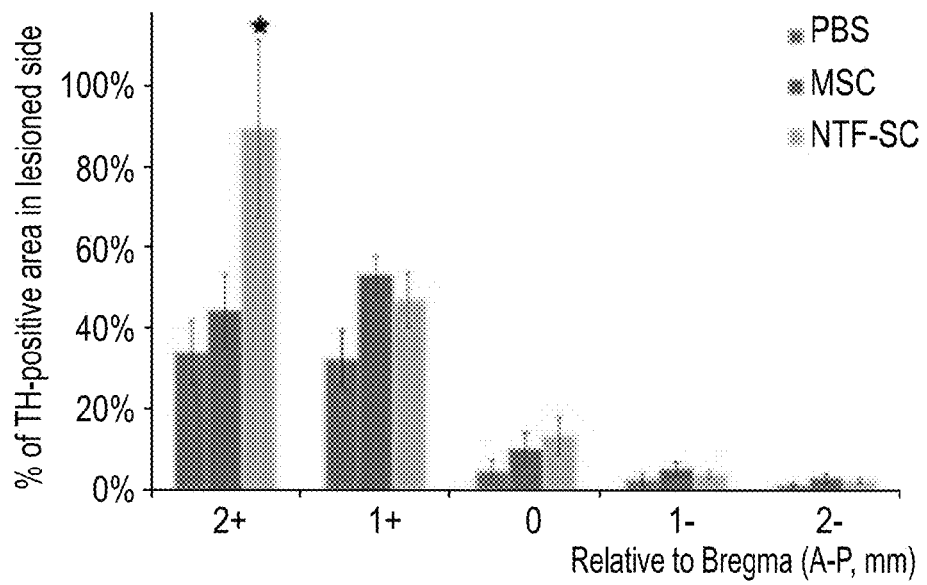
FIG. 7A
FIG. 7B
FIG. 7C
FIG. 7D
FIG. 7E

MESENCHYMAL STEM CELLS FOR THE TREATMENT OF CNS DISEASES

RELATED APPLICATIONS

This Application is a continuation of U.S. patent application Ser. No. 15/261,959 filed on Sep. 11, 2016 which is a division of U.S. patent application Ser. No. 14/556,281 filed on Dec. 1, 2014, now U.S. Pat. No. 9,474,787 which is a division of U.S. patent application Ser. No. 14/164,286 filed on Jan. 27, 2014, now U.S. Pat. No. 8,900,574 which is a division of U.S. patent application Ser. No. 12/994,761 filed on Nov. 25, 2010, now U.S. Pat. No. 8,663,987 which is a National Phase of PCT Patent Application No. PCT/IL2009/000525 having International Filing Date of May 26, 2009, which claims the benefit of priority of U.S. Provisional Patent Application No. 61/071,970 filed on May 28, 2008. The contents of the above Applications are all incorporated herein by reference.

FIELD AND BACKGROUND OF THE INVENTION

The present invention relates to cells and populations thereof which can be used for treating CNS diseases.

Parkinson's disease is an age-related disorder characterized by progressive loss of dopamine producing neurons in the substantia nigra of the midbrain, which in turn leads to progressive loss of motor functions manifested through symptoms such as tremor, rigidity and ataxia.

The use of stem cells as a cellular source in cell replacement therapy for Parkinson's disease has been suggested. Stem cells have the ability to exist in vivo in an undifferentiated state and to self-renew. They are not restricted to cell types specific to the tissue of origin, and so they are able to differentiate in response to local environmental cues from other tissues. This capability of self renewal and differentiation has great therapeutic potential in curing diseases.

U.S. Patent Appl. 20050265983 to the present inventors teaches human dopamine synthesizing MSCs which express neuronal markers and transcription factors that characterize midbrain DA neuron following induction of neuronal differentiation.

As an alternative to a dopamine replacement strategy, cell therapy may be aimed at restoring or reestablishing the normal anatomy (connectivity) and physiology (appropriate synaptic contacts and functioning) of the striatum. In this instance, the grafted cells have to survive and possess morphological electrophysiological and functional dopaminergic properties.

Neurotrophic factors (NTFs) are secreted proteins that regulate the survival, functional maintenance and phenotypic development of neuronal cells. Alterations in NTF levels are involved in triggering programmed cell-death in neurons and thus contribute to the pathogenesis of Parkinson's and other neurodegenerative diseases.

One of the most potent NTF for dopaminergic neurons is called glial cell line-derived neurotrophic factor (GDNF). It is known to promote the survival of the dopaminergic neurons in the substantia nigra, promote neurite outgrowth, increase cell body size and also raise levels of TH. GDNF belongs to a family of proteins, related to the TGF-β-superfamily, currently consisting of four neurotrophic factors: GDNF, Neurturin (NTN), Persephin, and Artemin/Neublastin. These factors are known to serve as regulators of cell proliferation and differentiation.

Various cells type produce GDNF including glia cells (oligodendrocytes and astrocyte), neuroblastoma and glioblastoma cell lines. It has recently been shown that rat BMSCs cultured in DMEM supplemented with 20% fetal bovine serum, at passage 6 express GDNF and NGF [Garcia R, et al., Biochem Biophys Res Commun. 316(3):753-4, 2004].

Administration of GDNF directly into the brain has been shown to be effective in various animal models of PD. In addition, exposure of cells to GDNF prior to transplant has proven beneficial. For instance, grafting of 400,000 fetal dopaminergic neurons prior to transplantation significantly improved the rotational behavior of lesioned rats [Mehta V, et al., J Neurosurg. 1999 April; 90(4):804-6].

Various methods have been used to aid administration of GDNF into the brain including osmotic pumps, capsules and microspheres. Another approach for GDNF delivery is in vivo gene therapy. Bone marrow mesenchymal cells genetically engineered to express GDNF, transplanted into MPTP-lesioned mice, were able to protect nigral neurons as well as striatal fibers [Park, K., Neurosci. Res. 40: 315-323, 2001].

Glutamate is the main excitatory amino acid neurotransmitter in the human central nervous system (CNS). It plays a major role in synaptic plasticity, learning, development, cognitive functions and human behavior. However, if not properly controlled glutamate may lead to detrimental results. Prolonged exposure to glutamate leads to over stimulation of excitatory a.a receptors, a process culminating in neuronal cell death.

Regulation of glutamate levels near and within the synaptic cleft is primarily performed by astrocytes. When extracellular glutamate levels are high, astrocytes can remove it from the synaptic space. Glutamate uptake is facilitated mainly by high affinity excitatory a.a transporters, which insert $Na^+$ and $H^+$ into the cell, while removing $K^+$ from the cell, thus enabling the transfer of glutamate into the cell against its electrochemical gradient. Although, the less common form of $Na^+$ independent transport also occurs.

Accumulating evidence implicate glutamate toxicity in the pathophysiology of several acute neurodegenerative processes, mainly cerebral ischemia and traumatic brain injuries. Furthermore, it appears that glutamate toxicity participates in chronic neurodegenerative disorders such as Huntington's disease (HD), Parkinson's disease (PD), amyotrophic lateral sclerosis (ALS), epilepsy and Alzheimer's disease (AD).

Reducing extracellular glutamate levels around the susceptible neurons affected by glutamate toxicity in the different disease modules may halt the neurodegenerative progression. A possible approach to provide such neuronal protection is by transplanting cells capable of performing glutamate uptake adjacent to the endangered neurons. Adult human mesenchymal stem cells (hMSC) obtained from bone marrow, may vary well prove to be a viable source for such transplantations.

Several studies have shown that MSCs following exposure to different factors in vitro, change their phenotype and demonstrate neuronal and glial markers [Kopen, G. C., et al., Proc Natl Acad USA. 96(19):10711-6, 1999; Sanchez-Ramos, et al. Exp Neurol. 164(2):247-56. 2000; Woodbury, D., J Neurosci Res. 61(4):364-70,2000; Woodbury, D., et al., J Neurosci Res. 69(6):908-17, 2002; Black, I. B., Woodbury, D. Blood Cells Mol Dis. 27(3):632-6, 2001; Kohyama, J., et al. Differentiation. 68(4-5):235-44, 2001; Levy, Y. S. J Mol Neurosci. 21(2):121-32, 2003].

WO2006/134602 teaches differentiation protocols for the generation of neurotrophic factor secreting cells.

WO2007/066338 teaches differentiation protocols for the generation of oligodendrocyte-like cells.

WO2004/046348 teaches differentiation protocols for the generation of neuronal-like cells.

SUMMARY OF THE INVENTION

According to an aspect of some embodiments of the present invention there is provided an isolated human cell comprising at least one mesenchymal stem cell phenotype and secreting brain-derived neurotrophic factor (BDNF), wherein a basal secretion of the BDNF is at least five times greater than a basal secretion of the BDNF in a mesenchymal stem cell.

According to an aspect of some embodiments of the present invention there is provided an isolated cell population comprising human mesenchymal stem cells, wherein at least 50% of the cells express glial fibrillary acidic protein (GFAP) and secrete at least one neurotrophic factor.

According to some embodiments of the invention, the at least one neurotrophic factor is glial cell line-derived neurotrophic factor (GDNF) or BDNF.

According to an aspect of some embodiments of the present invention there is provided an isolated cell population comprising human cells wherein:
 (i) at least N % of the human cells secreting brain-derived neurotrophic factor (BDNF), wherein a basal secretion of the BDNF is at least five times greater than a basal secretion of the BDNF in a mesenchymal stem cell;
 (ii) at least M % of the human cells comprise at least one mesenchymal stem cell phenotype; and
 (iii) at least one of the human cells secretes the BDNF and the at least one mesenchymal stem cell phenotype;
 where M and N are each independently selected between 1 and 99.

According to an aspect of some embodiments of the present invention there is provided a pharmaceutical composition comprising as an active agent the cell populations of the present invention, and a pharmaceutically acceptable carrier.

According to an aspect of some embodiments of the present invention there is provided a method of generating cells useful for treating a CNS disease or disorder, the method comprising:
 (a) incubating mesenchymal stem cells in a culture medium comprising platelet lysate to generate propagated mesenchymal stem cells; and
 (b) incubating the propagated mesenchymal stem cells in a differentiating medium, thereby generating cells useful for treating the CNS disease or disorder.

According to an aspect of some embodiments of the present invention there is provided an isolated cell generated according to the method of the present invention, having an astrocyte phenotype.

According to an aspect of some embodiments of the present invention there is provided an isolated cell generated according to the method of the present invention, having an oligodendrocyte phenotype.

According to an aspect of some embodiments of the present invention there is provided an isolated cell generated according to the method of the present invention, secreting dopamine.

According to an aspect of some embodiments of the present invention there is provided a method of generating cells secreting neurotrophic factors, comprising (a) incubating mesenchymal stem cells in a serum free medium comprising platelet lysate to generate propagated mesenchymal stem cells; and
 (b) incubating the propagated mesenchymal stem cells in a differentiating medium comprising at least one differentiating agent, the at least one differentiating agent being selected from the group consisting of platelet derived growth factor (PDGF), human neuregulin 1-β1, FGF2, EGF, N2, IBMX and cAMP, thereby generating cells secreting neurotrophic factors.

According to an aspect of some embodiments of the present invention there is provided a method of treating a CNS disease or disorder comprising administering to an individual in need thereof a therapeutically effective amount of a cell population generated according to the method described herein, thereby treating the CNS disease or disorder.

According to some embodiments of the invention, the isolated human cell takes up at least ten times more glutamate from its surroundings than a mesenchymal stem cell.

According to some embodiments of the invention, the isolated human cell is not genetically manipulated.

According to some embodiments of the invention, the cell population is non-genetically manipulated.

According to some embodiments of the invention, the isolated human cell further comprises an astrocytic structural phenotype.

According to some embodiments of the invention, the N % of the human cells comprise a structural phenotype.

According to some embodiments of the invention, the astrocytic structural phenotype is expression of at least one astrocytic marker.

According to some embodiments of the invention, the isolated human cell further expresses at least one additional neurotrophic factor.

According to some embodiments of the invention, the at least one additional neurotrophic factor is selected from the group consisting of glial derived neurotrophic factor (GDNF), neurotrophin-3 (NT-3), neurotrophin-4/5, Neurturin (NTN), Persephin, artemin (ART), ciliary neurotrophic factor (CNTF), insulin growth factor-I (IGF-1) and Neublastin.

According to some embodiments of the invention, the cell population further expresses at least one additional neurotrophic factor.

According to some embodiments of the invention, the at least one neurotrophic factor is GDNF.

According to some embodiments of the invention, the isolated human cell does not secrete nerve growth factor (NGF).

According to some embodiments of the invention, the isolated human cell takes up at least ten times more glutamate from its surroundings than a mesenchymal stem cell.

According to some embodiments of the invention, the mesenchymal stem cells comprise human mesenchymal stem cells and the platelet lysate comprises human platelet lysate.

According to some embodiments of the invention, the medium is devoid of xeno contaminants.

According to some embodiments of the invention, to duration of the incubating mesenchymal stem cells in a culture medium comprising platelet lysate is at least four weeks.

According to some embodiments of the invention, the culture medium is devoid of serum.

According to some embodiments of the invention, a percentage of the platelet lysate in the culture medium is about 5%.

According to some embodiments of the invention, a percentage of the platelet lysate in the culture medium is about 10%.

According to some embodiments of the invention, the CNS disease or disorder is a neurodegenerative disease or disorder.

According to some embodiments of the invention, the CNS disease or disorder is selected from the group consisting of a motion disorder, a dissociative disorder, a mood disorder, an affective disorder, an addictive disorder and a convulsive disorder.

According to some embodiments of the invention, the neurodegenerative disorder is selected from the group consisting of Parkinson's, multiple sclerosis, epilepsy, amyotrophic lateral sclerosis, stroke, autoimmune encephalomyelitis, diabetic neuropathy, glaucomatous neuropathy, Alzheimer's disease and Huntingdon's disease.

According to some embodiments of the invention, the cells comprise an astrocytic phenotype.

According to some embodiments of the invention, the cells comprise an oligodendrocytic phenotype.

According to some embodiments of the invention, the cells secrete at least one neurotransmitter.

According to some embodiments of the invention, the at least one neurotransmitter is dopamine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
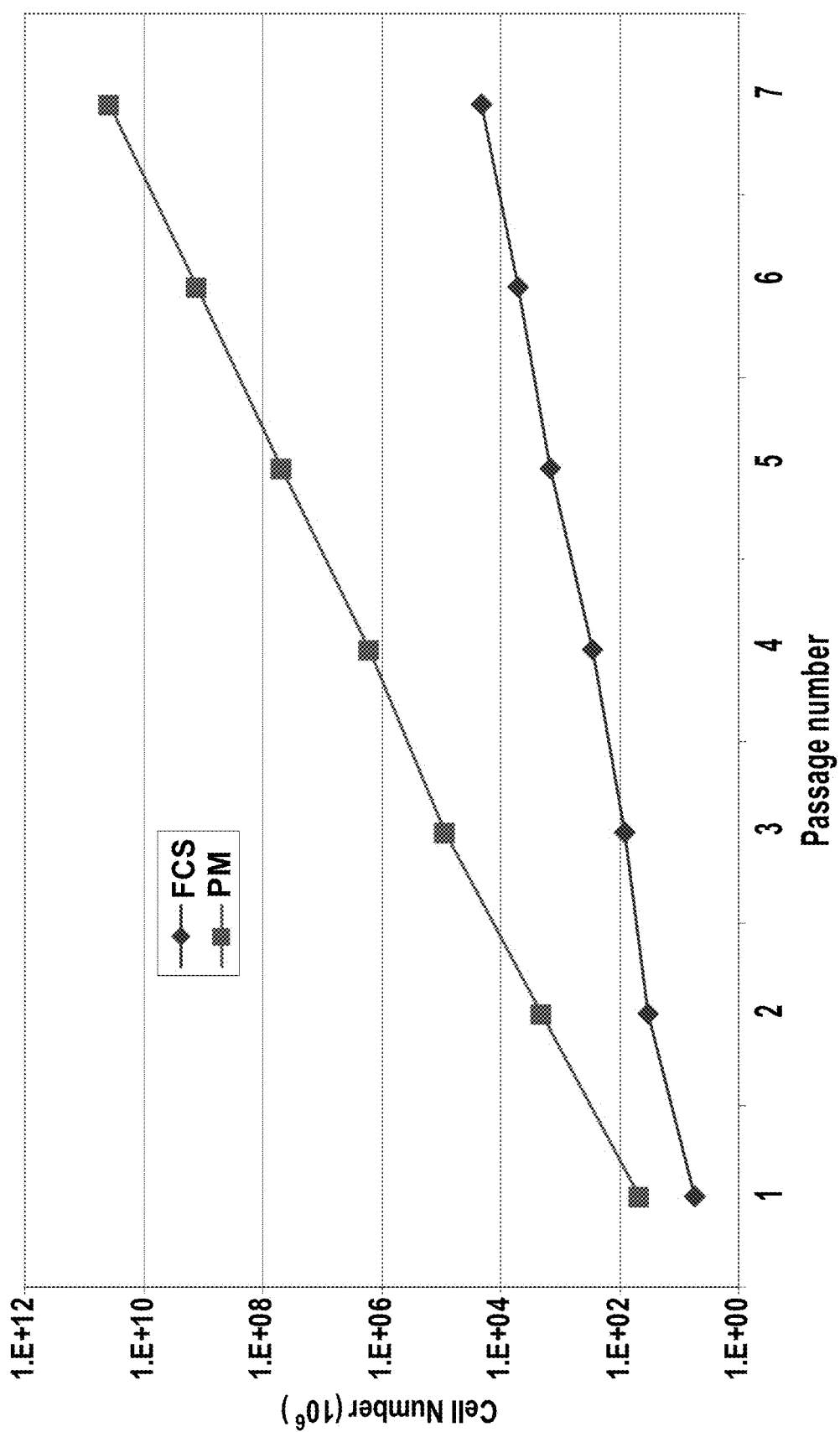

FIG. 1 is a graph illustrating the growth potential of MSC in medium containing 5% Platelet lysate (PM) as compared to MSC grown in medium containing 15% FCS (FCS). FIGS. 2A-2I are graphs illustrating the results of FACS analyses of plastic adherent MSC grown in 5% platelet lysate for approximately 4 weeks. The cells were negative for Hematopoetic surface markers: (CD3, T cell receptor; CD14 monocyte/macrophages; CD19, B cell marker; CD34 hematopoietic progenitors; CD45 pan-leukocyte marker, and HLA-DR) and stained positive for mesenchymal surface markers CD73, CD105 and CD90.

FIGS. 3A-3J are photomicrographs illustrating that human bone marrow derived MSC express and secrete neurotrophic factors. MSC and NTF-SC were stained with antibodies against neurotrophic factors including Brain Derived Neurotrophic Factor (BNDF) (A-B), Glial-Derived Neurotrophic factor (GDNF) (C-D) and Insulin-like growth factor 1 (IGF1) (E-F), and with antibodies against the astrocytic markers Glial fibrillary acidic protein (GFAP) (G-H) and Glutamine Synthetase (GS) (I-J). All secondary antibodies used were conjugated to Alexa-488 (green). Nuclei were visualized with DAPI (blue). Scale bar=50 μm.

Figure 3K:
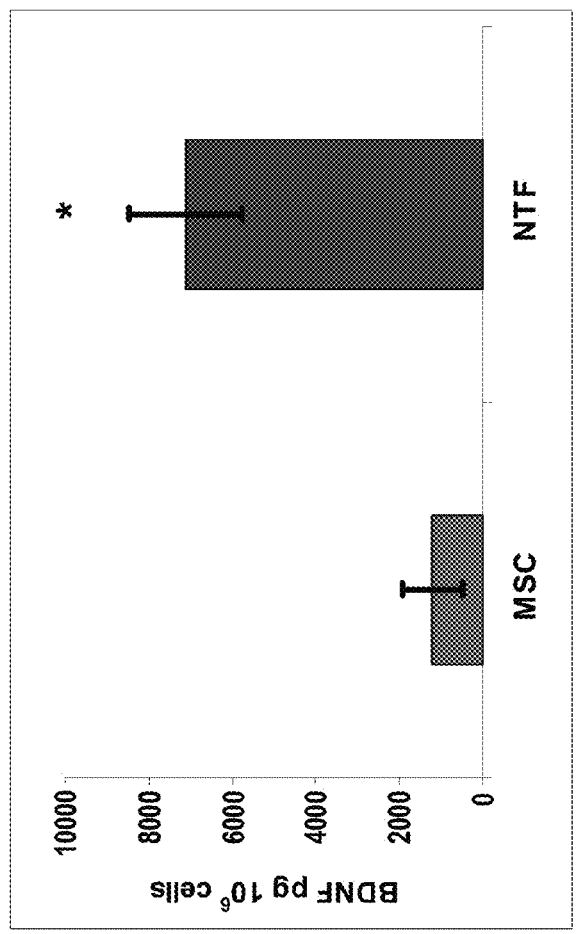
Figure 3L:
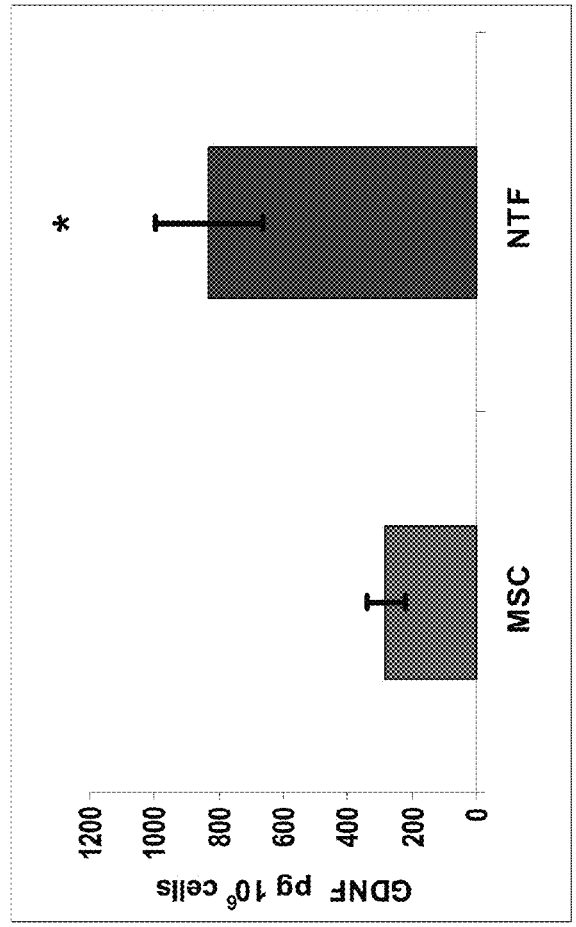

FIGS. 3K-3L are bar graphs illustrating the amount of neurotrophic factors secreted by the NTF-SCs of the present invention. Neurotrophic factor secretion was measured from human MSCs prior to and following induction of differentiation into NTF secreting cells, from 3 (BDNF) and 5 (GDNF) different donors analysed by ELISA assay. * $p<0.05$ for the MSC vs the NTF secreting cells (Student's t test). For BDNF (FIG. 3K): Donor 1: prior to differentiation=2666 pg/$10^6$ cells, following differentiation=9527 pg/$10^6$ cells; Donor 2: prior to differentiation=520 pg/$10^6$ cells, following differentiation=6903 pg/$10^6$ cells; Donor 3: prior to differentiation=463 pg/$10^6$ cells, following differentiation=4919 pg/$10^6$ cells.

Figure 4:
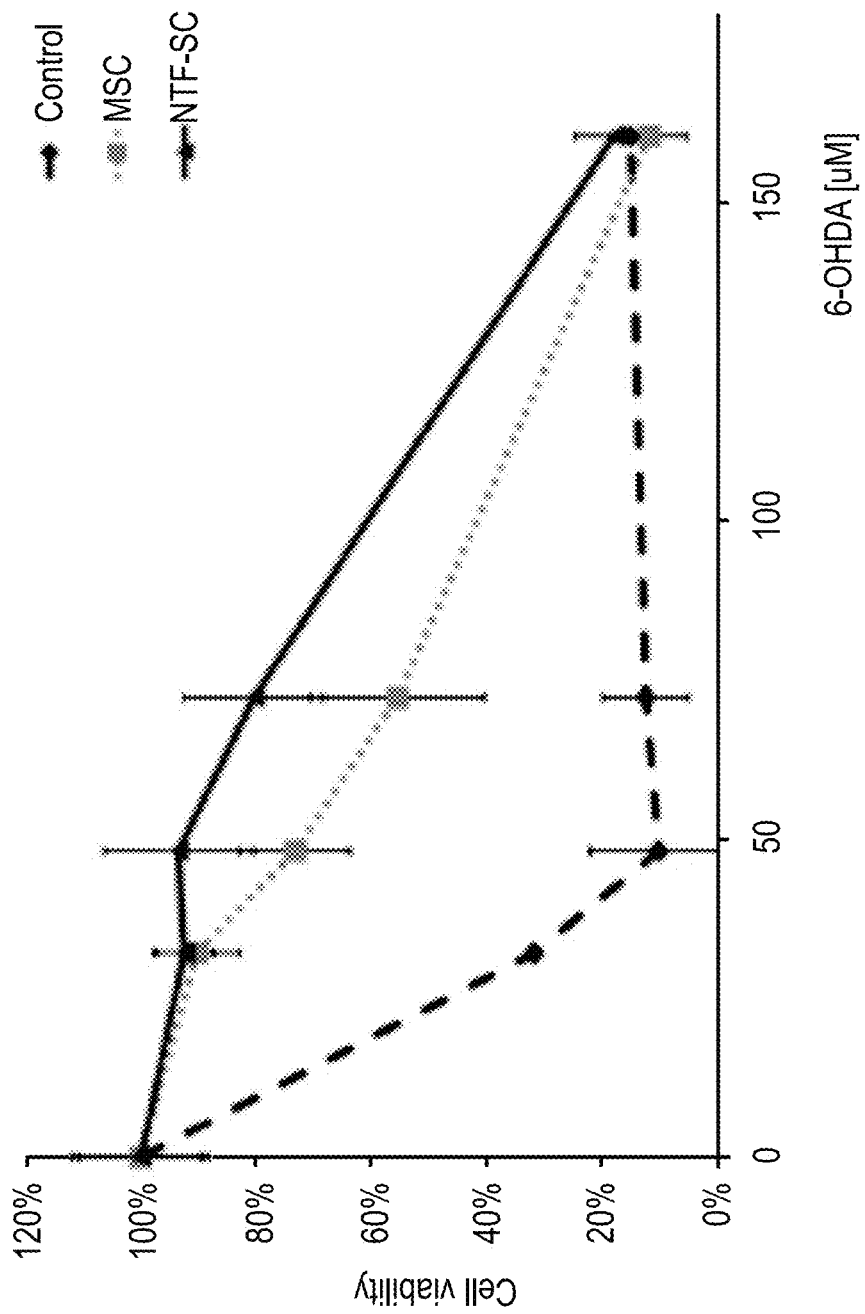

FIG. 4 is a graph illustrating that human MSC and NTF-SC media attenuated 6-OHDA induced neuroblastoma cells death. In the range of 32-160 μM, 6-OHDA treatment resulted in a survival rate of less than 35% compared to untreated SH-SYSY neuroblastoma cells. Media from both cell types of cells media attenuated the 6-OHDA induced cellular death in a statistically significant manner in comparison to neuroblastoma cells treated with 6-OHDA only ($p<0.05$ for the range of 32-72 μM). A treatment with 160 μM of 6-OHDA resulted in a smaller but statistically significant increase in cellular viability by the NTF-SC media only and not by MSC media.

FIGS. 5A-5B are graphs illustrating that striatal transplantation of human NTF-SC attenuate 6-OHDA-induced behavioral changes. (FIG. 5A) In the amphetamine induced rotations test only NTF-SC (n=20) treatment was beneficial compared to control (n=10) at two time points (day 28 and day 42). No statistically significant difference was shown for the MSC treated group (n=20) as compared to the control group or the NTF-SC treated group. In contrast, for the NTF-SC groups, a marked decrease of 25% and 45% after 14 and 28 days post transplantation was noted (FIG. 5B) 6-OHDA induced a hypoactive motor behavior pattern in an open field test at 7 days post treatment. NTF-SC treatment showed a positive effect in the voluntary mobility as compared to MSC- and PBS-treated groups (ANOVA, p=0.054).

FIGS. 6A-6E are illustrations and photographs illustrating the methodology of the stereological quantification of TH-positive striatal area in the lesioned rats. As depicted in FIG. 6C, striatal coronal sections were made into 40 μm sections, and every $8^{th}$ section was stained for thyrosine-hydroxylase (TH). Each section was captured by a X40 magnification and divided into 2-3 images from each side in a symmetrical fashion (FIGS. 6B, 6D). Using ImagePro software, a histogram based cutoff was determined and a mask was created (FIGS. 6A, 6E). The final quantification was performed by calculating the total red area in the masked images.

FIGS. 7A-7E are photographs and graphs illustrating that treatment with human NTF-SC salvaged TH-positive striatal terminals damaged by 6-OHDA. (FIGS. 7A-7C) a macro-view of TH staining in striatum with a representative slice for each group of rats (A-PBS, B-MSC, C-NTF-SC). (FIG. 7D) Digital quantification of the TH-positive area in the whole lesioned striatum as a percent of the untreated striatum, demonstrating the beneficial protective effect of NTF-SC treatment (n=4 from each group,|—P<0.05 compared to PBS). (FIG. 7E) quantification of TH positive area of the lesioned side compared to the untreated side—a segmental comparison. The whole striatum was divided into five segments from anterior to posterior (each group represent approximately 1 mm thickness of the striatum, *—p<0.05 compared to PBS).

FIGS. 8A-8G are images obtained following tracking of human NTF-SC by in-vivo MRI and corresponding histology. (FIG. 8A) T2* MRI scan conducted at 35 days post treatment of a control SPIOs-treated animal (without cells) demonstrating the SPIO injection site (blue circle) and the 6-OHDA injection site in the striatum (red circle). No other hypointense signals could be detected in the striatum. (FIG. 8B) The migratory pathway as demonstrated by an axial T2* weighted image. A marked hypointense signal is visible from the cell transplantation site (blue circle) to the 6-OHDA lesion site (red arrow). A good correlation to the Prussian blue staining was found (FIG. 8D) along the CC into the anterior striatum. The same trail (red arrow) can even be seen also in the T2 weighted image (FIG. 8C) which is less sensitive to the inhomogeniety induced by the SPIOs. (FIG. 8D) Prussian blue stain to detect SPIOs-labeled cells in an axial section (50 days after treatment in the animal that underwent MRI scan displayed in FIGS. 8B-8C) demonstrating a migratory path from the cell transplantation site (white arrow), along the corpus callosum (CC, hollow black arrows) and into the anterior striatum (STR, LV-lateral ventricle, scale bar ~500 μm). (FIGS. 8E-8G) Immunostaining with anti-human nuclei antibody of the marked white boxes in FIG. 8D in adjacent sections (scale bar 100 μm).

Figure 9:
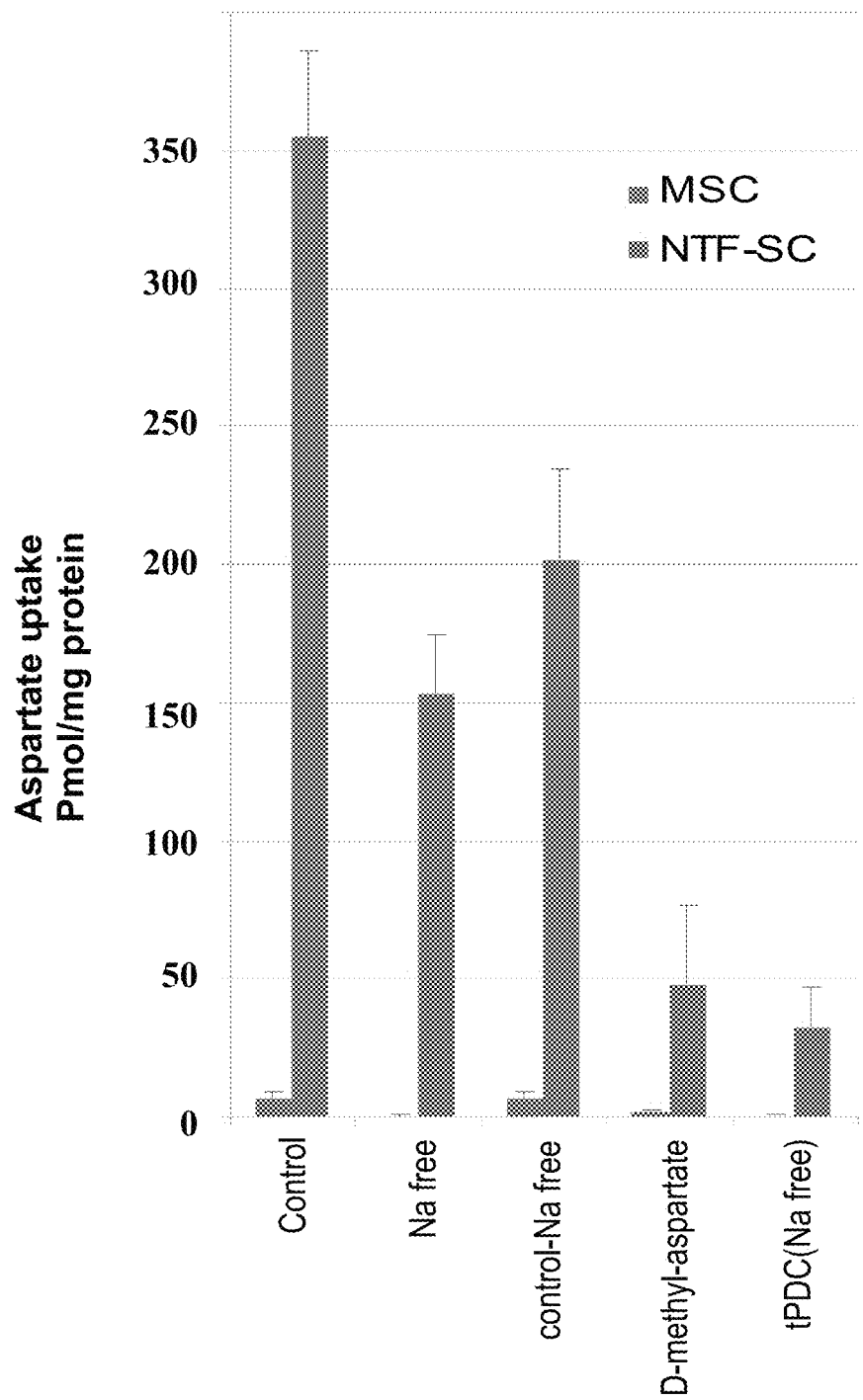

FIG. 9 is a bar graph illustrating that induction of MSC into NTF-SC increases glutamate uptake. [$^3$H]-D-aspartate uptake (50 nM) was measured in hMSC and in NTF-SC. Uptake was performed in the presence of Na$^+$ unless indicated otherwise. Na$^+$ dependent uptake was calculated by subtracting the results obtained from the Na free tests from the results of the control group. Competitive inhibition with D-methyl-aspartate (50 nM) was performed in the presence of [$^3$H]-D-aspartate at the same concentration as the other tests (50 nM). Inhibition with t-PDC, cells were preincubated with t-PDC for 15 minutes. NTF-SC perform glutamate uptake significantly better then MSC (P<0.0001). Inhibitors significantly decrease the uptake of glutamate in NTF-SC as compared with NTF-SC control (competitive inhibition P<0.0005, t-PDC P<0.0001).

Figure 10A:
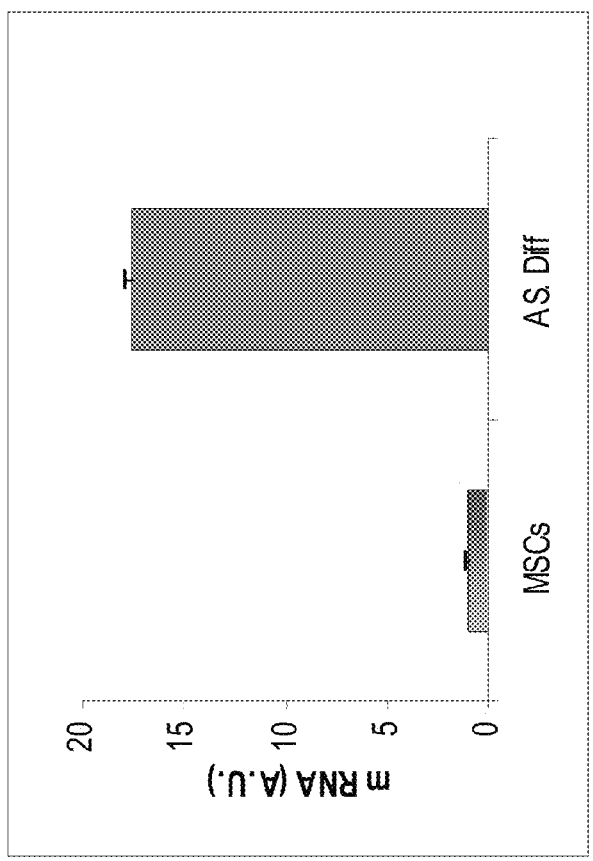
Figure 10B:
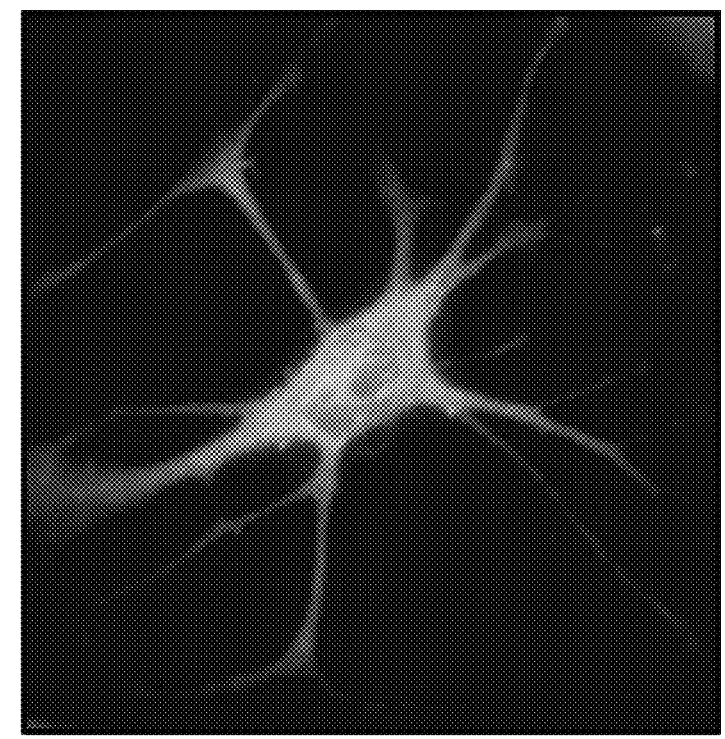
Figure 10:
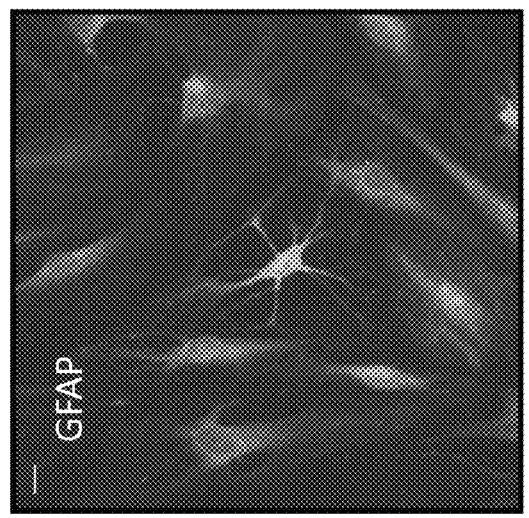

FIGS. 10A-10C are graphs and photomicrographs illustrating the expression of GFAP in the differentiated cells of the present invention, as measured by real-time RT-PCR (FIG. 10A) and immunocytochemistry (FIGS. 10B-10C).

Figure 11C:
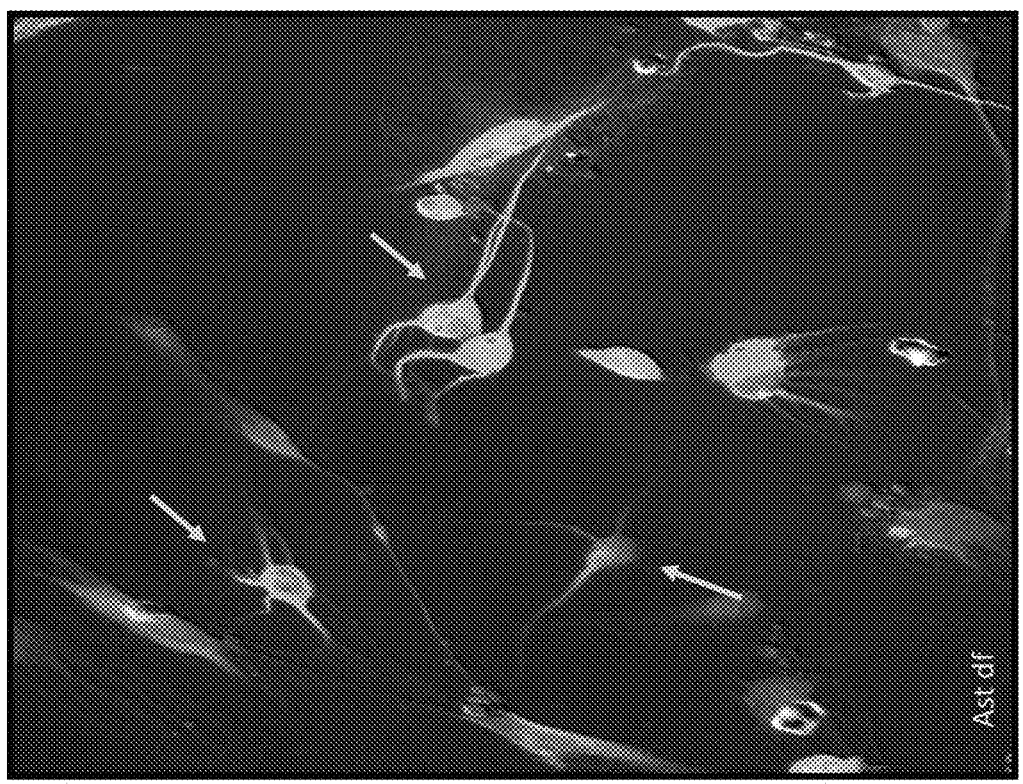
Figure 11B:
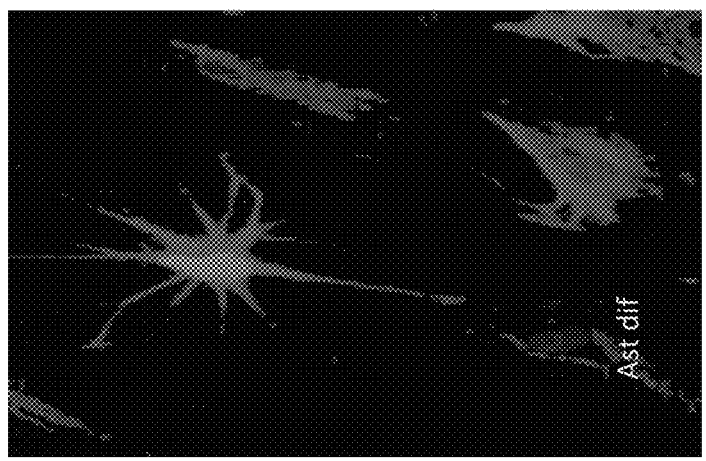
Figure 11A:
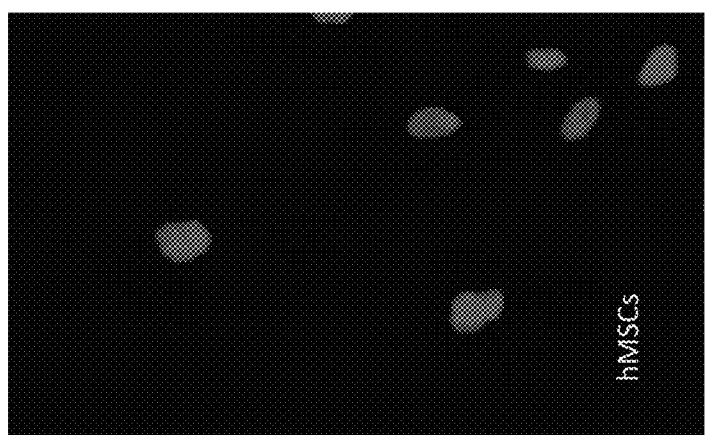

FIGS. 11A-11C are photomicrographs comparing the expression of S100 in non-differentiated (FIG. 11A) and differentiated (FIGS. 11B-11C) cells of the present invention.

DESCRIPTION OF SPECIFIC EMBODIMENTS OF THE INVENTION

The present invention relates to cells and populations thereof which can be transplanted into a patient in order to treat a myriad of neurodegenerative diseases.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Neurotrophic factors (NTFs) are secreted proteins that regulate the survival, functional maintenance and phenotypic development of neuronal cells. Alterations in NTF levels are involved in triggering programmed cell-death in neurons and thus contribute to the pathogenesis of Parkinson's disease and other neurodegenerative diseases.

One of the most potent NTF for dopaminergic neurons is called glial cell line-derived neurotrophic factor (GDNF). It is known to promote the survival of the dopaminergic neurons in the substantia nigra, promote neurite outgrowth, increase cell body size and also raise levels of TH. Another potent NTF for dopaminergic neurons is brain derived neurotrophic factor (BDNF). This NTF has potent effects on survival and morphology of dopaminergic neurons and its loss has been postulated to contribute to the death of these cells in Parkinson's disease (PD).

However, direct use of neurotrophic is prohibited as they do not pass the blood-brain barrier and do not distribute properly following systemic injection. Therefore, other strategies must be developed in order to take advantage of their therapeutic properties.

Protocols for differentiating human mesenchymal stem cells into neurotrophic factor secreting cells are known in the art—see for example WO 2006/134602.

Whilst searching for a way to increase the amount of neurotrophic factors secreted by mesenchymal stem cells, the present inventors have found that propagation of mesenchymal stem cells in platelet lysate prior to differentiation increased secretion of neurotrophic factors therefrom.

The present inventors have shown that MSCs differentiated following incubation in platelet lysate represent an astrocyte like shape accompanied by the presence of astrocyte markers. These cells were shown to express and secrete significant levels of GDNF and BDNF. Indeed, using immunocytochemistry procedures, the present inventors have shown that approximately 90% of the cells generated express GDNF, BDNF, S100, GFAP and glutamine synthetase (FIGS. 3A-3J, 10A-10C and 11A-11C).

Following transplantation into the striatum of 6-OHDA lesioned rat (a rodent model for Parkinson's) the cells survived for three months (as measured by MRI) and improved behavioral deficits examined by an open field test, and apomorphine induced rotational behavior. In addition, the cells were shown to reduce dopamine depletion and cause reinnervation of dopaminergic terminals. It was found that the efficacy of NTF-SC was superior to that of MSC in terms of behavioral, biochemical and histological indices. In addition, the present inventors demonstrated that the surviving cells migrated towards the lesion, and had the most significant effect at the end of the migration trail. Further, the present inventors showed that MSCs differentiated according to the protocols of embodiments of the present invention are capable of taking up glutamate.

Since the novel technology presented herein is clinically compatible and safe, the present inventors propose that the transplantation of NTF-SC derived from autologous human MSC should become an important option in treatment of neurodegenerative disorders.

Thus, according to one aspect of the present invention there is provided a method of generating cells useful for treating a neurodegenerative disorder, the method comprising:
(a) incubating mesenchymal stem cells in a culture medium comprising platelet lysate to generate propagated mesenchymal stem cells; and
(b) incubating the propagated mesenchymal stem cells in a differentiating medium, thereby generating cells useful for treating the neurodegenerative disorder.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage. The mesenchymal stem cells of the present invention may be of a syngeneic or allogeneic source, although the first is preferred.

According to a preferred embodiment of this aspect of the present invention the mesenchymal stem cells are not genetically manipulated (i.e. transformed with an expression construct) to generate the cells and cell populations described herein.

It will be appreciated that the cells of the present invention may be derived from any stem cell, although preferably not ES cells.

Mesenchymal stem cells may be isolated from various tissues including but not limited to bone marrow, peripheral blood, blood, placenta and adipose tissue. A method of isolating mesenchymal stem cells from peripheral blood is described by Kassis et al [Bone Marrow Transplant. 2006 May;37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006;24:1294-1301].

According to a preferred embodiment of this aspect of the present invention, the mesenchymal stem cells are human.

Bone marrow can be isolated from the iliac crest of an individual by aspiration. Low-density BM mononuclear cells (BMMNC) may be separated by a FICOL-PAGUE density gradient. In order to obtain mesenchymal stem cells, a cell population comprising the mesenchymal stem cells (e.g. BMMNC) may be cultured in a proliferating medium capable of maintaining and/or expanding the cells in the presence of platelet lysate. According to one embodiment the populations are plated on polystyrene plastic surfaces (e.g. in a flask) and mesenchymal stem cells are isolated by removing non-adherent cells. Alternatively mesenchymal stem cell may be isolated by FACS using mesenchymal stem cell markers.

Following isolation the cells are typically expanded by culturing in a proliferation medium capable of maintaining and/or expanding the isolated cells ex vivo in the presence of platelet lysate. The proliferation medium may be DMEM, alpha-MEM or DMEM/F12.

It will be appreciated that preferably when the mesenchymal stem cells are human, the platelet lysate is also obtained from human cells.

According to one embodiment, the medium is devoid of xeno contaminants i.e. free of animal derived components.

An exemplary mesenchymal stem cell isolation and propagation protocol is presented herein below.

Isolation of Human BM-MSC

Bone marrow samples (3-30 ml) were collected into EDTA containing tubes from the posterior iliac crest of adult human donors undergoing bone marrow aspiration in the course of diagnostic procedures. Bone marrow aspirates were diluted 1:1 with HBSS and mononuclear cells were separated by density centrifugation (1000× G for 20 min), over UNI-SEP MAXI (Polysucrose—Sodium Metrizoate) containing tubes. The mononuclear cell fraction was collected and washed in HBSS. Cells were re-suspended in Growth Medium containing 10% Platelet lysate (PM1), counted by the Trypan blue exclusion dye and seeded at a concentration of 250,000-350,000 cells/cm$^2$ in 75 cm$^2$ tissue culture flasks. Flasks were incubated in a 37° C. humidified incubator with 5% $CO_2$.

PM1 growth medium consisted of Dulbecco's Modified Eagle's Medium low glucose (Sigma, Aldrich), supplemented with 0.05 mg/ml Gentamycin (Sigma, Aldrich), 2 IU/ml Heparin (TRIMA), 0.001% 2-mercaptoethanol (Sigma, Aldrich), 1% non-essential essential amino acid solution (Sigma, Aldrich) and 10% platelet lysate. 24 hrs later PM1 medium was aspirated to remove non-adherent cells from the flask, adherent cells were washed gently with 10 ml of DMEM, and 10 ml of fresh PM1 were added to the flask. hMSC cells were allowed to proliferate for 12-18 days in PM1 medium, which was replaced twice weekly. After 12-18 days or when the flask reached confluence. The cells were harvested by removing all growth medium and incubating in TrypLE™ solution (Invitrogen) for 5 min in a 37° C. incubator. Cells are then washed in DMEM, counted, re-suspended in PM medium and seeded in CellStacks at a density of 500-3000 cells/cm$^2$.

PM growth medium consists of Dulbecco's modified eagle's medium low glucose supplemented with 0.05 mg/ml Gentamycin, 2 IU /ml Heparin and 5% platelet lysate. MSC cultures were passaged approximately every two weeks by detachment of the sub-confluent cell layer with TrypLE™ solution (Invitrogen). Experiments with the cells were performed after 2-7 passages. Accordingly, the cells were passaged for a minimum of two weeks in platelet lysate containing medium.

Platelet lysate may be prepared using any method known in the art. An exemplary freeze-thaw protocol is provided herein below.

Preparation of Platelet Lysate

Platelet Rich Plasma (PRP) may be from Blood Bank donations determined free of infectious agents (i.e. HIV, HTLV, HCV, HBsAg). PRP containing bags were stored at −80° C. and thawed in a 37° C. water bath. After thawing, the Platelet Rich Plasma of multiple donors was pooled, mixed and centrifuged at 14000× G for 10 minutes to remove platelet particles and membranes. The Platelet lysate supernatant was then collected and frozen at −80° C. until use. The Platelet lysate was tested for Endotoxin, Haemoglobin, pH, Total protein, Albumin, Osmolality Sterility and Mycoplasma.

Verification that the isolated (and optionally propagated) cell population comprises mesenchymal stem cells may be effected by identification of phenotypic and functional criteria. The phenotypic criteria include the expression of specific surface antigens: CD73, CD90 and CD105 (>=95% positive) and the absence (<2%) of (T-cells), CD14 (Monocyte surface marker), CD19 (B cells), CD34 (Hematopoietic stem cells), CD45 (Hematopoietic cells), and HLA-DR (Human Class II Histocompatibility antigen). The surface expression of these cells may be analyzed using methods known in the art—for example by Flow Cytometry.

Exemplary antibodies that may be used to verify the presence of mesenchymal stem cells include CD73 PE conjugated (BD Pharmingen), CD90 PE-Cy5 conjugated (eBioscience) CD105 PE conjugated (Beckman Coulter) CD14 FITC conjugated (eBioscience) CD19 PE-Cy5 conjugated (eBioscience) CD34 FITC conjugated (Beckman Coulter), CD45 PE conjugated (eBioscience) and HLA-DR PE-Cy5 conjugated (BD Pharmingen).

Another method for verifying the presence of mesenchymal stem cells is by showing that the cells are capable of differentiating into multi-lineages such as for example adipocytes, osteocytes and chondrocytes. This may be effected for example using Human Mesenchymal Stem Cell Functional Identification Kit (R&D Systems).

As mentioned, following propagation of mesenchymal stem cells in a platelet lysate containing medium, the cells may be differentiated in a differentiating medium to generating cells useful for treating a neurodegenerative disorder.

It will be appreciated that the components of the differentiating medium are selected according to the cell phenotype required.

Thus according to one embodiment, the phenotype may be astrocyte-like cells.

As used herein the phrase "astrocyte-like cells" refers to cells comprising at least one astrocytic phenotype which allows same to in vivo mediate an astrocytic activity, i.e., support of neurons.

Such phenotypes are further described hereinbelow.

Differentiation to astrocyte-like cells can be effected by incubating the MSCs in differentiating media such as those described in U.S. Pat. No. 6,528,245 and by Sanchez-Ramos et al. (2000); Woodburry et al. (2000); Woodburry et al. (J. Neurisci. Res. 96:908-917, 2001); Black and Woodbury (Blood Cells Mol. Dis. 27:632-635, 2001); Deng et al. (2001), Kohyama et al. (2001), Reyes and Verfatile (Ann. N. Y. Acad. Sci. 938:231-235, 2001) and Jiang et al. (Nature 418:47-49, 2002).

WO2006/134602, incorporated herein by reference, teaches differentiation protocols for the generation of neurotrophic factor secreting cells.

According to one embodiment in order to generate astrocyte like cells, MSCs are initially incubated in a medium comprising epidermal growth factor hEGF (e.g. 20 ng/ml) and/or basic fibroblast growth factor (e.g. 20 ng/ml) in the presence or absence of N2 supplement (insulin, progesterone, putrescin, selenium and transferrin). Following this the BMScs may be differentiated in a second medium comprising platelet derived growth factor (e.g. 5 ng/ml) and human neuregulin 1-β1 (e.g. 50 ng/ml). This "differentiating medium" may also include differentiating agents such as IL-1β and/or dbcAMP.

According to one embodiment, the MSCs are incubated in each differentiating medium for at least 24 hours. It will be appreciated that longer culturing times are contemplated, such as two days, three days, four days or more.

According to another embodiment, the components of the differentiating medium are selected so as to generate cells comprising an oligodendrocyte phenotype. The differentiating media may be DMEM or DMEM/F12, or any other medium that supports neuronal growth. According to a preferred embodiment of this aspect of the present invention, the medium is Neurobasal medium (e.g. Cat. No. 21103049, Invitrogen, Ca, U.S.A.). Table 1 herein below, summarizes various differentiation protocols for the generation of oligodendrocytes.

TABLE 1

| Stage | Medium$^a$ | Days |
|---|---|---|
| Control | | |
| | Regular growth medium:<br>α-MEM<br>FCS 15%<br>L-glutamine 2 mM<br>Penicillin 100 U/ml<br>Streptomycin 100 ug/ml<br>Nystatin 12.5 U/ml | 13 |
| Protocol A | | |
| Differentiating Medium (A) | Neurobasal medium<br>N2 supplement<br>B27 supplement<br>bFGF 10 ng/ml<br>GGF 50 ng/ml<br>db-cAMP 1 nM | 13 |
| Protocol B | | |
| Additional Medium (B) | Neurobasal medium<br>PDGF 20 ng/ml<br>NT-3 10 ng/ml<br>Il-1β 20 ng/ml | 5 |
| Differentiating Medium (B) | Neurobasal medium<br>N2 supplement<br>NT-3 10 ng/ml<br>Il-1β 20 ng/ml | 8 |
| Protocol C | | |
| Additional Medium (C) | Neurobasal medium<br>TH 30 ng/ml<br>(stock 20 ug/ml)<br>RA 1 μM<br>GGF 50 ng/ml | 5 |
| Differentiating Medium (C) | Neurobasal medium<br>TH 30 ng/ml<br>(stock 20 ug/ml)<br>RA 1 μM<br>NT-3 10 ng/ml | 8 |
| Protocol D | | |
| Additional Medium (D) | Neurobasal medium<br>PDGF 20 ng/ml<br>GGF 50 ng/ml | 5 |
| Differentiating Medium (D) | Neurobasal medium<br>Shh 300 ng/ml<br>NT-3 10 ng/ml<br>db-cAMP 1 nM<br>Forskolin 5 μM | 8 |

WO2007/066338, incorporated herein by reference, teaches differentiation protocols for the generation of oligodendrocyte-like cells.

According to another embodiment, the components of the differentiating medium are selected so as to generate cells that secrete dopamine.

An exemplary method for differentiating mesenchymal stem cells into neurotransmitter (e.g. dopamine) secreting cells is detailed in Table 2, herein below.

TABLE 2

| Stage 1:<br>Additional<br>differentiation<br>medium | DMEM/F12 (without HEPES); 2 mM L-glutamine;<br>SPN; 10 ng/ml human basic fibroblast growth factor<br>(bFGF); 10 ng/ml EGF; *N2 supplement; 40 μM<br>arachidonic acid; 10-40 μM docosahexaenoic acid |
|---|---|

TABLE 2-continued

| | |
|---|---|
| (24-72 hr) | (DHA); 40 µM Vit-E; 10 ng/ml fibroblast growth factor 8 (FGF8); 200 ng/ml sonic hedgehog (Shh) |
| Stage 2: Dopaminergic differentiation medium (12-96 hr) | DMEM/F12; 2 mM L-glutamine; SPN; *N2 supplement; 200 µM ascorbic acid; 1 mM dibutyryl cyclic AMP; 0.5 mM isobutylmethlxanthine; 1 µM retinoic acid; 200 µM butylated hydroxyanisole (BHA); human transforming growth factor β3 (TGF- β3), 2 ng/ml; human galia-derived neurotrophic factor: (GDNF), 2 ng/ml; human neurturin: (hNTN), 20 ng/ml; human brain-derived neurotrophic factor: (BDNF), (10 ng/ml; human neurotrophin: (hNT-3), 20 ng/ml; human interleukin-1β (hIL-1β), 100 pg/ml; |

WO2004/046348, incorporated herein by reference, teaches differentiation protocols for the generation of neuronal-like cells.

It will be appreciated that any of the differentiating media may comprise other agents such as neurotrophic factors (e.g. BDNF, CNTF, GDNF, NTN, NT3 or LIF), hormones, growth factors (e.g. GGF2, TGF-β3, TGF-α, FGF-8 and bFGF), vitamins, hormones e.g., insulin, progesterone and other factors such as sonic hedgehog, bone morphogenetic proteins, forskolin, retinoic acid, ascorbic acid, putrescin, selenium and transferrin.

As mentioned, the present inventors showed that propagation of mesenchymal stem cells in platelet lysate prior to incubation with a differentiating agent which steers the mesenchymal stem cell towards an astrocytic phenotype (e.g. platelet derived growth factor (PDGF), human neuregulin 1-β1, FGF2, EGF, N2, IBMX and cAMP), generated cells capable of secreting large amounts of neurotrophic factors.

Thus, according to another aspect of the present invention, there is provided an isolated human cell comprising at least one mesenchymal stem cell phenotype and secreting brain-derived neurotrophic factor (BDNF), wherein a basal secretion of the BDNF is at least five times greater than a basal secretion of the BDNF in a mesenchymal stem cell.

The term "isolated" as used herein refers to a cell that has been removed from its in-vivo location (e.g. bone marrow, neural tissue). Preferably the isolated cell is substantially free from other substances (e.g., other cell types) that are present in its in-vivo location.

The mesenchymal stem cell phenotypes which are comprised in the cells of the present invention are typically structural. For example, the cells of the present invention may show a morphology similar to that of mesenchymal stem cells (a spindle-like morphology). Alternatively or additionally the cells of the present invention may express a marker (e.g. surface marker) typical to mesenchymal stem cells but atypical to native astrocytic cells. Examples of mesenchymal stem cell surface markers include but are not limited to CD105+, CD29+, CD44+, CD90+, CD34−, CD45−, CD19−, CD5−, CD20−, CD11B− and FMC7−. Other mesenchymal stem cell markers include but are not limited to tyrosine hydroxylase, nestin and H-NF.

As mentioned, the basal secretion of BDNF from cells according to this aspect of the present invention is at least five times greater than a basal secretion of the BDNF in a non-differentiated mesenchymal stem cell.

It will be appreciated that the basal secretion of BDNF may be even higher, such as at least six times greater, at least seven times greater, at least eight times greater, at least nine times greater or even at least ten times greater.

According to one embodiment, at least 50%, at least 60%, at least 70%, at least 80%, at least 90% or more of a population of the differentiated cells of the present invention express BDNF.

As used herein the term "basal secretion" refers to a secretion which does not involve addition of stimulants. The non-differentiated mesenchymal stem cell is typically obtained from the same source as the differentiated mesenchymal stem cell and is identical thereto apart from having been differentiated according to the protocols described herein. Thus typically, the non-differentiated mesenchymal stem cell is in an identical medium to the differentiated mesenchymal stem cells but without the addition of differentiating agents.

According to one embodiment the cells of the present invention are capable of taking up glutamate from their surrounding milieu (e.g. culture medium). For example, the cells of the present invention may be capable of taking up at least 10 times, at least 20 times, at least 30 times, at least 40 times or even at least 50 times more glutamate from their surroundings than a non-differentiated mesenchymal stem cell.

The cells of the present invention may also comprise an astrocytic phenotype.

As used herein, the phrase "astrocytic phenotype" refers to a structural and/or functional parameter typical (e.g. unique) to an astrocyte which may be used to distinguish between the differentiated MSCs of the present invention and non-differentiated MSCs. The astrocytic phenotype may comprise a single or a number of features which may be used to distinguish between the differentiated MSCs of the present invention and non-differentiated MSCs.

It will be appreciated that the functional parameters may overlap with the structural parameter e.g., presence of secretory vesicles.

According to one embodiment the functional astrocytic phenotype comprises the ability to express an additional neurotrophic factor.

As used herein the term "express" refers to the synthesis and/or secretion of the above-mentioned neurotrophic factor.

As used herein, the phrase "neurotrophic factor" refers to a cell factor that acts on the cerebral nervous system comprising growth, differentiation, functional maintenance and/or survival effects on neurons. Examples of neurotrophic factors include, but are not limited to, glial derived neurotrophic factor (GDNF), GenBank accession nos. L19063, L15306; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession no. AAC39640; brain derived neurotrophic factor, (BDNF), GenBank accession no. CAA42761; artemin (ART), GenBank accession no. AAD13110; ciliary neurotrophic factor (CNTF), GenBank accession no. NP_000605; insulin growth factor-I (IGF-1), GenBank accession no. NP_000609; and Neublastin GenBank accession no. AAD21075.

According to one embodiment, at least 50%, at least 60%, at least 70%, at least 80%, at least 90% or more of a population of the differentiated cells of the present invention express GDNF.

Typically the cells of the present invention do not secrete nerve growth factor (NGF).

Examples of structural astrocytic phenotypes include a cell size, a cell shape, an organelle size and an organelle number. Thus, astrocytic structural phenotypes include a round nucleus, a "star shaped" body and many long processes that end as vascular foot plates on the small blood vessels of the CNS. Further examples of structural astrocytic phenotypes may be found in the following materials: Reynolds and Weiss, Science (1992) 255:1707-1710; Reynolds, Tetzlaff, and Weiss, J. Neurosci (1992) 12:4565-4574; and Kandel, et al., Principles of Neuroscience, third ed. (1991), Appleton & Lange, Norwalk, Conn. These structural phenotypes may be analyzed using microscopic techniques (e.g. scanning electro microscopy). Antibodies or dyes may be used to highlight distinguishing features in order to aid in the analysis.

A structural astrocytic phenotype may also comprise expression of an astrocyte marker.

As used herein the phrase "astrocyte marker" refers to a polypeptide which is either selectively or non-selectively expressed in an astrocyte. The astrocyte marker may be expressed on the cell surface or internally. Examples of astrocyte markers include S100 beta, glial fibrillary acidic protein (GFAP), glutamine sythetase (GS), GLAST and GLT1.

According to one embodiment, at least 50%, at least 60%, at least 70%, at least 80%, at least 90% or more of a population of the differentiated cells of the present invention express at least one or more astrocyte markers including, but not limited to S100 beta, GFAP and GS.

It will be appreciated that cell populations obtained according to the methods describe herein are typically non-homogeneous.

Thus according to another aspect of the present invention there is provided an isolated cell population comprising human cells wherein:
  (i) at least N % of the human cells secreting brain-derived neurotrophic factor (BDNF), wherein a basal secretion of the BDNF is at least five times greater than a basal secretion of the BDNF in a mesenchymal stem cell;
  (ii) at least M % of the human cells comprise at least one mesenchymal stem cell phenotype; and
  (iii) at least one of the human cells secretes the BDNF and the at least one mesenchymal stem cell phenotype;
  where M and N are each independently selected between 1 and 99.

M % may be any percent from 1% to 99% e.g. 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%.

N % may be any percent from 1% to 99% e.g. 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%.

The percentage of cells which secrete BDNF may be raised or lowered according to the intended needs. This may be effected by FACS using an antibody specific for an astrocyte cell marker. Examples of such astrocytic markers are described hereinabove. If the cell marker is an internal marker, preferably the FACS analysis comprises antibodies or fragments thereof which may easily penetrate a cell and may easily be washed out of the cell following detection. The FACS process may be repeated a number of times using the same or different markers depending on the degree of enrichment and the cell phenotype required as the end product.

According to another embodiment of this aspect of the present invention the cell populations may be enriched for cells comprising both an astrocytic phenotype and a mesenchymal stem cell phenotype such that a homogeneous population of cells are generated.

Once differentiated and optionally isolated, the cells may be tested (in culture) for their ability to secrete a BDNF. An exemplary method for analyzing secretion of BDNF (and other neurotrophic factors (NTFs) is described herein below.

ELISA for Secreted NTFs

For analysis of secreted NTFs, supernatant is collected from cultures of MSCs or of NTF-secreting cells at the end of the differentiation procedure described above, and cells are harvested and counted. The amount of NTFs such as Glial Derived Neurothrophic Factor, (GDNF) or Brain Derived Neurotrophic Factor (BDNF) in the cell's culture supernatants was quantified by using a GDNF or BDNF ELISA assay (GDNF DuoSet DY212; BDNF DuoSet DY248; R&D Systems) according to the manufacture's protocol.

As mentioned according to the phenotype, the cells and cell populations of the present invention may be used to treat a particular disease or disorder. The cell populations may be used directly following differentiation or may be enriched for a particular phenotype as described hereinabove. As summarized in Table 3 hereinbelow, certain neurotrophic factors or set of neurotrophic factors have been shown to be particularly beneficial for treating a particular disease. For example, cells of the present invention which secrete BDNF and GDNF would be particularly suitable for treating Parkinson's.

TABLE 3

| Disease | Astrocytic phenotype | REF |
| --- | --- | --- |
| Parkinsons | BDNF, FGF, GDNF | Walker D G, et al. Brain Res 1998; 794: 181-7. |
| | | Lorigados L, et al. Rev Neurol 1998; 26: 744-8. |
| | | Mogi M, et al. Neurosci Lett 1994; 180: 147-50. |
| | | Howells D W, et al. Exp Neurol 2000; 166: 127-35. |
| | | Beck K D, et al. Nature 1995; 373: 339-41. |
| | | Tomac A, et al. Nature 1995; 373: 335-9. |
| | | Gash D M, et al. Nature 1996; 380: 252-5. |
| | | Choi-Lundberg D L, Science 1997; 275: 838-41. |
| | | Bozzi Y, Borrelli E. Eur J Neurosci 1999; 11: 1275-84. |
| | | Chauhan N B, et al Soc Neurosci Abstr 1998; 24: 1465. |
| | | Chauhan N B, et al, Neurology 1999; 52: A212-213. |

TABLE 3-continued

| Disease | Astrocytic phenotype | REF |
|---|---|---|
| Epilepsy | BDNF, NT-3, glutamate transporter | G. W. Mathern, Mol. Chem. Neuropathol. 30 1-2 (1997), pp. 53-76.<br>Lucia Tapia-Arancibia et al. Frontiers in Neuroendocrinology 2004 July; 25(2): 77-107.<br>RYUTA KOYAMA and YUJI IKEGAYA; NEUROSCIENCE UPDATE 2005 August; 11(4): 282-7.<br>Gerald Seifert, et al., Nature Reviews Neuroscience 7, 194-206 (March 2006). |
| ALS | NT3, IGF1, BDNF, glutamate transporter | Luis H. Et al., Brain Research Reviews 2004 December; 47(1-3): 263-74.<br>Bradley W G. Ann Neurol 1995; 38: 971.<br>Haase G, et al. Nat Med 1997; 3: 429-36.<br>Arakawa Y, J Neurosci 1990; 10: 3507-15. |
| Drug and alcohol addiction | GDNF | Ron D, Janak P H. Rev Neurosci. 2005; 16(4): 277-85. |
| Brain injury | Ability of cells to respond to IL-1 | Nancy Rothwell; Brain, Behavior, and Immunity. 2003 June; 17(3): 152-7. |
| Alzheimers | BDNF | Crutcher K A, et al. J Neurosci 1993; 6: 2540-50.<br>Scott S A, et al. Nerve growth factor in Alzheimer's disease: increased levels throughout the brain coupled with declines in nucleus basalis. J Neurosci 1995; 15: 6213-21.<br>Peng S, et al. J Neuropathol Exp Neurol 2004; 63: 641-9.<br>Murer M G, et al. Neuroscience 1999; 88: 1015-32. |
| Huntingdon's | BDNF, NT-3, or NT-4/5 | Martinez-Serrano A, Bjorklund A. Trends Neurosci 1997; 20: 530-8.<br>Perez-Navarro E, et al. J Neurochem 2000; 75: 2190-9.<br>Perez-Navarro E, et al. Neuroscience 1999; 91: 1257-64. |
| Schizophrenia | NT-3, BDNF | Gal Shoval, Abraham Weizmana; Eur Neuropsychopharmacol. 2005 May; 15(3): 319-29.<br>Levi-Montalcini, R., 1987. Biosci. Rep. 7, 681-699.<br>Hattori, M., Nanko, S., 1995. Biochem. Biophys. Res. Commun. 209, 513-518.<br>Virgos, C., 2001, Schizophr. Res. 49, 65-71. |
| Optic nerve | CNTF | Paul A. Sieving, et al., Proc Natl Acad Sci USA. 2006 Mar. 7; 103(10): 3896-901. |
| Stroke | FGF, BDNF | Wu D; Neuro Rx. 2005 January; 2(1): 120-8. |

It has been proposed that astrocyte cells may reduce the oxidative stress in neurons by metabolizing dopamine, as they express monoamine oxidase-B and catechol-O-methyltransferase. Additionally, it has been proposed that astrocyte cells may be capable of preventing NO generated neurotoxicity by a glutathione dependent mechanism (Chen et al. 2004, Curr Drug Targets. 2005 Nov;6(7):821-33). Accordingly, cells of the present invention which comprise a scavenging function and/or express dopamine metabolizing enzymes may also be suitable for treating Parkinson's.

Owing to insufficient clearance or decrease of the glutamate transporters glutamate excitotoxicity has been suggested as a causative factor for ALS [Bendotti 2001, et al, J Neurochem, 79(4):737-746, 2001]. Thus cells of the present invention which show an elevated glutamate transporter activity may also be suitable for treating ALS.

It will be appreciated that cells capable of secreting neurotransmitter such as dopamine would be particularly suitable for treating Parkinson's disease.

Further, cells comprising an oligodendrocyte phenotype would be particularly suitable for diseases and conditions of the nervous system that result from the deterioration of, or damage to, the myelin sheathing generated by myelin producing cells are numerous. Myelin may be lost as a primary event due to direct damage to the myelin or as a secondary event as a result of damage to axons and neurons. Primary events include neurodegenerative diseases such as multiple sclerosis (MS), human immunodeficiency MS-associated myelopathy, transverse myelopathy/myelitis, progressive multi focal leukoencepholopathy, central pontine myelinolysis and lesions to the myelin sheathing (as described below for secondary events). Secondary events include a great variety of lesions to the axons or neurons caused by physical injury in the brain or spinal cord, ischemia diseases, malignant diseases, infectious diseases (such has HIV, Lyme disease, tuberculosis, syphilis, or herpes), degenerative diseases (such as Parkinson's, Alzheimer's, Huntington's, ALS, optic neuritis, postinfectious encephalomyelitis, adrenoleukodystrophy and adrenomyeloneuropathy), schizophrenia, nutritional diseases/disorders (such as folic acid and Vitamin B12 deficiency, Wernicke disease), systemic diseases (such as diabetes, systemic lupus erthematosis, carcinoma), and toxic substances (such as alcohol, lead, ethidium bromide); and iatrogenic processes such as drug interactions, radiation treatment or neurosurgery.

Thus, according to another aspect of the present invention there is provided a method of treating a CNS disease or disorder.

As used herein, the phrase "CNS disease" refers to any disorder, disease or condition of the central nervous system which may be treated with the cells of the present invention.

Accordingly, these cells can be used for preparing a medicament (interchangeably referred to as pharmaceutical composition), whereby such a medicament is formulated for treating a CNS disease or disorder.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, ALS, Multiple Sclerosis, Huntingdon's disease, autoimmune encephalomyelitis, diabetic neuropathy, glaucomatous neuropathy, macular degeneration, action tremors and tardive dyskinesia, panic, anxiety, depression, alcoholism, insomnia, manic behavior, Alzheimer's and epilepsy.

In any of the methods described herein the cells may be obtained from any autologous or non-autologous (i.e., allogeneic or xenogeneic) human donor. For example, cells may be isolated from a human cadaver or a donor subject.

The cells of the present invention can be administered to the treated individual using a variety of transplantation approaches, the nature of which depends on the site of implantation.

The term or phrase "transplantation", "cell replacement" or "grafting" are used interchangeably herein and refer to the introduction of the cells of the present invention to target tissue. The cells can be derived from the recipient or from an allogeneic or xenogeneic donor.

The cells can be grafted into the central nervous system or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation.

Intraparenchymal transplantation can be effected using two approaches: (i) injection of cells into the host brain parenchyma or (ii) preparing a cavity by surgical means to expose the host brain parenchyma and then depositing the graft into the cavity. Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20., 1976), by removing bone overlying the brain and stopping bleeding with a material such a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated and the astrocytic phenotype comprised in the cell (e.g. particular neurotrophic factor being secreted) by the cells of the present invention. For example, cells secreting GDNF are preferably implanted in the substantia nigra of a Parkinson's patient.

Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu MZ, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu MZ, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002;13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest. Thus, for example the cells may be administered directly into the brain as described hereinabove or directly into the muscle as described in Example 3 hereinbelow.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, 6-OHDA-lesioned mice may be used as animal models of Parkinson's. In addition, a sunflower test may be used to test improvement in delicate motor function by challenging the animals to open sunflowers seeds during a particular time period.

Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

Survival and rotational behavior (e.g. on a rotarod) of the animals may be analyzed following administration of the cells of the present invention.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p.1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA. Additionally, the cells of the present invention may be co-administered with other cells capable of synthesizing a neurotransmitter. Such cells are described in U.S. Pat. Appl. No. 20050265983 to the present inventors.

Following transplantation, the cells of the present invention preferably survive in the diseased area for a period of time (e.g. at least 3 months), such that a therapeutic effect is observed.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984); "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996) and Parfitt et al. (1987). Bone histomorphometry: standardization of nomenclature, symbols, and units. Report of the ASBMR Histomorphometry Nomenclature Committee. J Bone Miner Res 2 (6), 595-610; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation and Characterization of Neurotrophic-Factor-Secreting Cells (NTF-SCs)

Materials and Methods

Preparation of Platelet Lysate

Platelet lysate was prepared using a freeze-thaw protocol. Platelet Rich Plasma (PRP) were obtained from Blood Bank donations determined free of infectious agents (i.e. HIV, HTLV, HCV, HBsAg). PRP containing bags were stored at −80° C. and thawed in a 37° C. water bath. After thawing the Platelet Rich Plasma of multiple donors was pooled, mixed and centrifuged at 14000× G for 10 minutes to remove platelet particles and membranes. The Platelet lysate supernatant was then collected and frozen at −80° C. until use. The Platelet lysate was tested for endotoxin, haemoglobin, pH, total protein, albumin, osmolality, sterility and mycoplasma.

Isolation and Proliferation of Human MSC:

Adult human bone marrow samples were collected from the posterior iliac crest of adult human donors, undergoing bone marrow aspiration, after obtaining informed consent. Bone marrow aspirates were diluted 1:1 with Hanks' Balanced Salt Solution (HBSS, Biological Industries, Beit-Haemek, Israel) and mononuclear cells were separated by density centrifugation, over UNI-SEP$_{max}$/UNI-SEP+(Polysucrose—Sodium Metrizoate, NovaMed, Jerusalem, Israel) containing tubes. The mononuclear cell fraction was collected, washed in HBSS and centrifuged. Cells were re-suspended in Growth Medium 1, counted and seeded at a concentration of 250,000-350,000 cells/cm$^2$ in 75 cm$^2$ tissue culture flasks (Corning, N.Y., USA). Flasks were incubated in a 37° C. humidified incubator with 5% $CO_2$.

Growth medium 1 consisted of Dulbecco's Modified Eagle's Medium (DMEM, Biological Industries), supplemented with 100 µg/ml streptomycin, 100 U/ml penicillin, 12.5 units/ml nystatin (SPN, Biological industries), 2 mM L-Glutamine (Biological industries), 2 IU/ml Heparin (Trima, Kibutz Maabarot, Israel), 0.001% 2-mercaptoethanol (Sigma-Aldrich, St. Louis, Mo., USA), 1% MEM non-essential amino acid solution (Biological Industries) and 10% Platelet lysate. Platelet lysate was processed from frozen-thawed human platelet rich plasma (PRP) as described herein above. 24 hrs later, Growth medium 1 was aspirated to remove non-adherent cells from the flask. Human MSC were allowed to proliferate in Growth medium 1, which was replaced twice weekly. After 12-18 days the cells were trypsinized (trypsin from Biological Industries), centrifuged, counted, resuspended in Growth medium 2 and seeded in CellStacks (Corning) at a density of 500-3000 cells/cm$^2$. Growth medium 2 consists of DMEM supplemented with SPN, glutamine and heparin as in Growth medium 1 and 5% PRP. MSC cultures were passaged approximately every two weeks. Experiments on the cells were performed after 2-7 passages.

Induction of Human MSC into NTF-SC

Human MSC (12,000 cells/cm$^2$) were first placed in DMEM supplemented with SPN, 2 mM L-Glutamine (Biological industries), 20 ng/ml human epidermal growth factor (hEGF), 20 ng/ml human basic fibroblast growth factor (hbFGF) (R&D Systems) and N2 supplement (Invitrogen). After 72 hours, the medium was replaced with DMEM supplemented with 1 mM dibutyryl cyclic AMP (dbcAMP), 0.5 mM isobutylmethylxanthine (IBMX) (Sigma-Aldrich), 5 ng/ml human platelet derived growth factor (PDGF), 50 ng/ml human neuregulin 1-β1/HRG1-β1 EGF domain and 20 ng/ml hbFGF (all from R&D Systems) for 3 more days.

Immunocytochemistry

Human MSC and NTF-SC were fixed with 4% paraformaldehyde and stained with rabbit anti-glial fibrillary acidic protein (GFAP;1:200, DAKO), rabbit anti glutamine synthetase (GS; 1:100; Sigma), rabbit anti-GDNF (1:100, Santa Cruz), rabbit anti-BDNF (1:100, Santa Cruz), rabbit anti IGF-1 (1:100, Santa Cruz). Secondary antibodies were goat anti-rabbit Alexa-488 (1:200, Molecular Probes). For GDNF staining, secondary antibodies were biotinylated goat anti-rabbit (1:200; Jackson Laboratories) and streptavidine-Alexa-488 (1:200, Molecular Probes). Nuclear DNA was stained by 4,6-diamino-2-phenylindole (DAPI) (1:1000, Sigma).

In-Vitro Neuroprotection Assay

Neuroblastoma cell line SH-SYSY cells (ATCC, Manassas, Va., USA) were grown in basal media consisting of DMEM with 10% fetal calf serum (FCS), 2 mM L-glutamine, and SPN (Biological industries). The SH-SYSY cells were plated in 96-well plates. Each well was applied with either human MSC or NTF-SC conditioned media or with serum free medium (DMEM, Glutamine and SPN), and immediately exposed to oxidative insult by 6-OHDA (Sigma-Aldrich) for 24 hours. Cell viability after treatments was analyzed by adding 3-(4, 5-dimethylthiazole-2-yl)-2, 5-diphenyltetrazolium bromide (MTT) solution to each well followed by incubation at 37° C. for 3 hours. Absorbance was determined at 564 nm in a microplate reader. Cell viability was evaluated in sextuplets for each treatment and compared to the serum free treated cells.

ELISA Based Measurements of NTFs Secretion

At the end of the NTF-SC induction process, the cell culture supernatant was measured for human GDNF and BDNF concentrations by a sandwich ELISA procedure according to the manufacturer's instructions (DuoSet, R&D System for human BDNF and GDNF). The absorbance at 450 nm and 570 nm was recorded on a Microplate Reader (Labsystems Multiscan MS). The results were calculated for one million cells.

Results

Analysis of MSC in Medium Containing 5% Platelet Lysate

The growth potential of MSC in medium containing 5% Platelet lysate (PM) as compared to MSC grown in medium containing 15% FCS (FCS) is demonstrated in FIG. 1.

FACS analyses of plastic adherent MSC grown in 5% platelet lysate for approximately 4 weeks is demonstrated in FIGS. 2A-2I. The cells were negative for Hematopoetic surface markers: (CD3, T cell receptor; CD14 monocyte/macrophages; CD19, B cell marker; CD34 hematopoietic progenitors; CD45 pan-leukocyte marker, and HLA-DR) and stained positive for Mesenchymal surface markers CD73, CD105 and CD90.

Induced Human NTF-SC Express Neurotrophic Factors

In-vitro analysis of the NTF-SC revealed their NTF expression profile. They expressed astrocyte markers such as GFAP and GS. Moreover, The NTF-SC highly expressed the GDNF, BDNF and IGF-1 proteins as indicated by immunocytochemistry (FIGS. 3A-3J). ELISA analysis showed that the differentiated NTF-SC secrete the neurotrophic factors into the culture supernatant. While untreated MSC secreted low levels of BDNF and GDNF (1216±725 pg/10$^6$ cells and 337±27 pg/10$^6$ cells, respectively), after six days of induction the NTF-SC secreted over five times more BDNF (7117±1335 pg/10$^6$ cells), and over twice the amount of GDNF (787±206 pg/10$^6$ cells) (FIGS. 3K-3L).

NGF was found to be negative when tested in supernatants of 7 different MSCs donors propagated in PM and in 6 different supernatants of NTF-secreting cells, using the ELISA kit to Human bNGF (DuoSet R&D, limit of Detection—2 pg/ml, linear between 4 and 250 pg/ml).

Conditioned Media from Human NTF-SC Protect Neuroblastoma Cell Line against 6-OHDA Toxicity:

The protective effect of the induced MSC in vitro, was examined using a neuroblastoma cell line, SH-SY5Y, exposed to increasing doses of 6-OHDA (32-160 μM). For the neuroprotection assay, human MSCs were induced, following which the induction medium was removed. The induced cells were then incubated with fresh serum free medium for an additional 24 hours to allow secretion of NTFs. For controls, supernatants of untreated MSC incubated in serum free medium for 24 h were used. The SH-SY5Y cells were incubated with the supernatants and one hour later, 6-OHDA neurotoxin was added to the cultures. Cell viability was measured 24 hours later, using MTT. A consistent reduction in viability of the SH-SY5Y cells incubated with DMEM and 32, 48 and 72 μM of 6-OHDA (31.7±6.9%, 10.1±0.2% and 12.3±0.4%, respectively, FIG. 4) was noted. In contrast, SH-SY5Y cells that were incubated with supernatants, collected from untreated MSC or NTF-SC media, demonstrated a statistically significant higher percentage of viability in the presence of 32, 48 and 72 μM 6-OHDA. The NTF-SC media demonstrated an added protective value upon the survival of the SH-SY5Y cells, although no statistically significant difference was demonstrated between the induced NTF-SC media treatment and the untreated MSC media treatment (90.2±7.4%, 73.2±9.6% and 55.4±15.9%, respectively for the MSC group, p<0.05, and 92.4±5.0%, 93.4±12.9% and 80.3±12% for the NTF-SC group, p<0.005, FIG. 4). At 160 μM 6-OHDA, cell viability dropped to 15.0±0.6% in the control group and similarly in the MSC group (11.7±0.2%), while the NTF-SC media remained slightly beneficial (17.9±0.6%, P<0.05 compared to both groups).

Example 2

In-Vivo Studies with the NTF-SCs of the Present Invention

Materials and Methods

6-OHDA Induced Striatal Lesion

A total of 63 male Sprague-Dawley rats weighting 260-300 gr (Harlan, Jerusalem, Israel) were used in this experiment. They were placed under 12 hours light/12 hours dark conditions and grown in individual ventilated cages (IVC) with ad libitum access to food and water.

7 µg/2.5 µl/site of 6-hydroxy dopamine (6-OHDA, Sigma-Aldrich) was injected into two sites (total of 14 µg 6-OHDA) in the right striatum according to the rat brain atlas (43) in 56 animals. Under chloral hydrate anesthesia the rats were placed in a digital stereotactic frame (Stoelting, Wood Dale, Ill., USA) and 6-OHDA was injected to the following coordinates (relative to the bregma and dura): AP +0.5 ML 2.5 DV −6.0 & AP −0.5 ML 4.2 DV −6.0 at a rate of 1 µl/minute using a Hamilton 701 N syringe. The inserted needle was withdrawn from each location after 5 minutes.

Stem Cell Transplantation

Human MSCs grown in serum free conditions for 6 days or induced NTF-SC, were used. On treatment day, the cells were trypsinized, washed with phosphate buffered saline (PBS) and counted. Two concentrations of cells were injected (50,000 cells/µl or 150,000 cells/µl in PBS). A total of 150,000 or 450,000 cells/3 µl were injected per site at a rate of 1 µl/minute, and cells were transplanted into two sites along the same DV axis: AP −1.8, ML 4.6, DV −5 and −7. Cells viability was assessed by trypan blue (Sigma-Aldrich) after each transplantation session.

Study Design

The in-vivo experiment was performed on the 6-OHDA induced striatal lesion model. Cells, or PBS as control, were transplanted on the same day of the 6-OHDA injections, 50 minutes later, posterior to the lesion within the treated striatum. The experiment consisted of the following groups: the control group was treated with 6-OHDA and with PBS instead of cellular treatment (n=10); MSC treated groups were treated with either a high dose (450,000 cells, n=10) or a low dose (150,000 cells, n=11) of serum free medium treated MSC; NTF-SC group was treated with either high dose (450,000 cells, n=10) or low dose (150,000 cells, n=11) of induced NTF-SC. Another group of untreated animals (n=7) were used as controls for the open field test.

For cell tracking purposes three different time points were analyzed by using histology based study or in-vivo MRI. At the first time point, 7 days post cellular treatment, 4 animals that were treated with high dose NTF-SC were sacrificed for histological evaluation only. For the second time point, on the 35$^{th}$ day, we conducted an in-vivo MRI study on selected animals. These animals (n=3 from the control group and n=3 from the low dose NTF-SC treated group) were treated with cells that were pre-labeled with super-paramagnetic iron oxide particles (SPIOs, 5 µg/ml, Feridex, Advanced magnetic, Cambridge, Mass., USA). SPIOs were incubated with poly-L-lysine (1 µg/ml medium, 70-150 KD, Sigma-Aldrich) for one hour before adding to the medium on the last day of stage 1 medium treatment. Cultures were washed with stage 2 medium of induction after 24 hours. The control group was treated with 1 µg of SPIOs in 6 µl of PBS (the same volume of the cell suspension). The last time point for cell tracking was at the end of the experiment, at 50 days after treatment day.

Immunosuppression was induced by daily subcutaneous administration of 15 mg/Kg cyclosporine A (Novartis, Basel, Switzerland), starting one day prior to cellular treatment and continued throughout the experiment. Animals received prophylactic antibiotic treatment with Enrofloxacin (50 mg/Kg, Bayer, Germany) for five days from the first day of the experiment.

Behavioral Tests

D-Amphetamine-induced rotational behavior was measured for 90 minutes following i.p. administration of 2.5 mg/Kg (Sigma-Aldrich) using an automated Rotameter device (San Diego Instruments, San-Diego, Calif., USA). The net ipsilateral rotations were measured at 14, 28 and 42 days post cell transplantation.

Open field test was conducted at 7 days post treatment by introducing the animals into a 50 cm$^2$ arena and videotaping the spontaneous behavior of the rats for 30 minutes. The images were analyzed by EthoVision 3 software (Noldus, The Netherlands).

MRI

Anesthesia was induced with 4% isoflurane in 95% O$_2$, and maintained with ~1-2% isoflurane (Vetmarket ltd., Petah-Tikva, Israel) at a flow rate of ~1 liter/minute. Respiratory rate was monitored throughout all the experiments. Body temperature was maintained by circulating water at 37° C. MRI scans were performed on a 7.0 T/30 cm Bruker Biospec equipped with a gradient system capable of producing gradient pulses of up to 400 mT/m (Bruker Biospin, Karlsruhe, Germany). A body coil was used as the transmit coil, and a rat quadurature coil was used as the receiving coil. MRI experiments were performed on the 35th day post transplantation and 6-OHDA injection. Scans included: T$_2$ weighted images (WI) RARE8 (TR/TE=3500/75 ms). The field of view (FOV) was 2.56×2.56, the matrix size was 256×128 zero filled to 256×256, and a slice thickness of 700 µm was chosen, 15 slices were collected. Additionally, three dimensional (3D) gradient echo (GE) images were collected (FLASH, TR/TE=150/14 ms, flip angle=15°) with a FOV of 2.56×2.56×0.48 and a matrix size of 128×96×24 (zero filled to 128×128×32), resulting in a spatial resolution of 200× 200×150 (µm)$^3$. The images are presented as raw data without any image processing.

Immunohistochemistry

At the end of the experiment (7 or 50 days post treatment) animals were transcardially perfused with ice cold PBS following a solution of 4% paraformaldehyde and 4% sucrose in phosphate buffer (PB) according to a known protocol (NeuroScience Labs, NSA, Knoxville, Tenn.). Brains were immersed in the perfusion solution for 24 hours in 4° C. following cryoprotection in 30% sucrose for additional 48 hours before freezing. 12 samples were processed by NSA (4 of the PBS group, 4 of the high MSC group, 4 of the high NTF-SC group and 4 animals treated with high dose of NTF-SC cells that were sacrificed after a week). These samples were serially sectioned into 40 µm coronal sections and every 8$^{th}$ section throughout the striatum was dyed for human nuclei antigen and the adjacent section for tyrosine hydroxylase (TH).

The brains of animals treated with SPIOs labeled cells were sectioned axially (8 µm) and dyed with Prussian blue stain (Sigma-Aldrich, according to manufacturer instructions) for the detection of Fe particles. Adjacent sections were immunostained with anti human nuclear antibody. Briefly, sections were microwave-boiled in a citrate buffer for antigen unmasking, and then immersed in a blocking and permeability solution (10% fetal calf serum, 2% bovine serum albumin, 1% glycine and 0.05% Triton). Post blocking, the samples were incubated overnight with anti human nuclear antibody (1:200) in 4° C. Sections were dyed with anti mouse IgG conjugated to Alexa Fluor 568 (Invitrogen, 1:500). Nuclei were counterstained with DAPI (1:500, Sigma-Aldrich). CD68 staining (1:500, Serotec, Oxford, UK) was conducted in a similar manner except the antigen unmasking process and the use of biotinilated anti mouse IgG (ready to use, Zymed-Invitrogen) followed by streptavidin Alexa Fluor 568 (1:500, Invitrogen).

Stereological Study

All sections stained for TH (n=4 animals from each group) were quantified for the area with a positive stain in the striatum. By using an Olympus DP71 camera (Japan) at a X40 magnification, 2-3 images were photographed to cover all or almost all the striatum of each side and each animal. The images were then quantified by the ImagePro 5.1 software that measured the total area of positive staining, according to a unified cutoff. The operator of the software was blind to the origin of the images. The damage was calculated as the percent of the TH-positive area in the lesioned striatum divided by the TH-positive area of the untreated contralateral side.

Dopamine Measurements by HPLC

Animals (n=5 each of the following groups: PBS, high dose MSC and high dose NTF-SC) were sacrificed by $CO_2$ and their brains were quickly removed and placed on ice. The striatae were dissected out and weighted. Each sample was sonicated in ice cold 1 ml of 0.1 M perchloric acid until homogeneity was achieved. The samples were centrifuged for 15 minutes (12,000 rpm, 4° C.), and the supernatants were collected and transferred onto a 0.2 µm nylon filter tubes (Corning). The samples were centrifuged again (6,000 rpm, 5 minutes, 4° C.) and the filtrates were stored in −80° C. until analyzed. An aliquot of the filtrate was injected into the HPLC system (Waters, Milford, Mass., USA) equipped with a C18 reverse phase, 3µ LUNA column (100 mm×2 mm, Phenomenex, Torrance, Calif., USA). The sample was eluted by a mobile phase made of 25 mM $NaH_2PO_4$, 50 mM Na-citrate, 0.03 mM EDTA, 10 mM diethylamine HCl and 2.2 mm sodium octyl sulphate (pH 3.2), 30 ml/L methanol and 22 ml/L dimethylacetamide at a flow rate of 0.4 ml/min. The dopamine peak was determined by electrochemical detection at a potential of 0.6 V. The dopamine content in the sample was calculated by extrapolating the peak area from a standard curve (range 1-200 pg of dopamine) constructed under the same conditions during each run by the Maxima Workstation (Waters). The results were normalized to the sample weight.

Statistical Analysis

The results are expressed as means±standard error. Student's t-test was used to compare means of two groups. Comparisons between several groups were done by ANOVA with Scheffe's post-hoc analysis. Repeated tests (amphetamine-induced rotations) were also analyzed by repeated ANOVA test. Statistical calculations were performed using SPSS v. 13.

Results

Transplanted Human NTF-SC Attenuate 6-OHDA Induced Rotational Behavior in Rats

Overall, the treated animals of all groups tolerated well the various therapies including immunosuppression. Of 56 animals, 2 died within the experimental follow up, one of peritonitis, and the other of an unknown cause. The animals failed to gain weight for 14 days post treatment, regardless of the group tested (excluding healthy controls for the open field test), and from that point on, almost all animals gained weight in a similar manner.

The control (PBS) group demonstrated a statistically significant increase of amphetamine-induced ipsilateral rotations on the $14^{th}$ day post lesion (2.71±0.79 net ipsilateral rotations per minute) and the $28^{th}$ day (4.11±0.86), reaching a plateau on the $42^{nd}$ day measurement (4.74±1.07) suggesting that the pathological process of death of nigrostriatal dopaminergic nerve terminals was progressive in nature for at least 28 days.

There were no statistically significant differences between the different cell doses, regardless of the type of treatment and the day of measurement. In the untreated MSC low dose group it was found that the animals rotated at a rate of 3.54±0.63, 2.61±0.55 and 3.25±0.75 net ipsilateral turns per minute on days 14, 28 and 42 post treatment respectively, while the MSC high dose treated group showed lower but not statistically significant measures: 2.05±0.41, 2.22±0.52 and 2.30±0.78 at the same time intervals. The NTF-SC treated group had shown the same trait between the doses: 1.19±0.6, 1.29±0.44 and 2.07±0.81 in the low dose treated group compared to 2.12±0.42, 1.49±0.32 and 1.67±0.52 in the high dose treated group. Hence, the high and low dose groups were combined for another statistical analysis. It was found that both cellular treatment types produced a non-progressing effect on the rotational behavior. The NTF-SC group demonstrated a lower result in the first measurement fourteen days post-treatment, although it not statistically significant different from the other groups. It had a statistically significant better result than the control group on the two later measurements (2.45±0.54 and 2.86±0.54 for the combined MSC treated group on days 28 and 42 post treatment, respectively, compared to 1.46±0.37 and 2.16±0.37 for the combined NTF-SC treated group at the same time intervals, p<0.05 compared to the PBS group). In summary, the MSC treated group did not demonstrate a statistically significant improvement as compared to the control (PBS) group. In contrast, for the cells undergoing the novel induction based treatment, the NTF-SC groups, a marked decrease of 25% and 45% after 14 and 28 days post transplantation was noted (FIG. 5A).

All 6-OHDA treated animals demonstrated overall motor hypoactivity in the open field test on the $7^{th}$ day post treatment. The control group activity indices were similar to those of the MSC treated group. The total distance walked by the combined low and high dose NTF-SC treated animals was 3667 cm on average, which was 22% higher compared to the control group (2989 cm) and 17% higher than the combined low and high dose MSC treated group (3119 cm) on average. However, there was no statistically significant difference between the groups (p=0.054) (FIG. 5B).

Transplantation of Human NTF-SC Resulted in a Greater Preservation of TH-Positive Area in the 6-OHDA Lesioned Striatum The methodology of the stereological study is illustrated in FIGS. 6A-6E. It was found that 6-OHDA-induced lesions with this specific protocol decreased the striatal TH-positive area by more than 5-fold in comparison to the control hemisphere (15.26±2.95% of the contralateral striatum). Both types of cellular treatment, MSC and NTF-SC, demonstrated a protective effect. However, only the NTF-SC yielded a statistically significant higher TH-positive area as a percent of the untreated side (31.15±6.27%), by increasing it more than twice in comparison to the control group, while MSC treatment failed to induce a statistically significant difference (23.11±3.5%, FIGS. 7A-7D).

Interestingly, when subdividing the different areas of the striatum into sections of approximately 1 mm thick, it was found that the NTF-SC were beneficial in the anterior, rather than the posterior area of the striatum, the region of transplantation (FIG. 7E).

Cellular Transplantation Inhibited 6-OHDA-Induced Dopamine Depletion in the Lesioned Striatae It was found that both types of cellular treatments, i.e. MSC and NTF-SC, prevented the falls of striatal dopamine levels induced by neurotoxin injection by more than 2.5-fold compared with the control group (HPLC measurement of the levels of dopamine in the whole lesioned striatum, was defined as a percentage of the untreated side). While the control group (n=5) lesioned striatae contained only 21.3±3.8% dopamine measured in comparison to the untreated side, MSC treated animals (n=5) had on average 68.7±8.6% and the NTF-SC treated group (n=5) had 72.4±16.4% striatal dopamine levels compared to the intact contralateral striatum. Only measurements from the NTF-SC treated group reached a statistically significant difference compared to the control group (p<0.05).

Tracking of Transplanted Cells by Histology and in-Vivo MRI

Figures 8A, 8B, 8C:
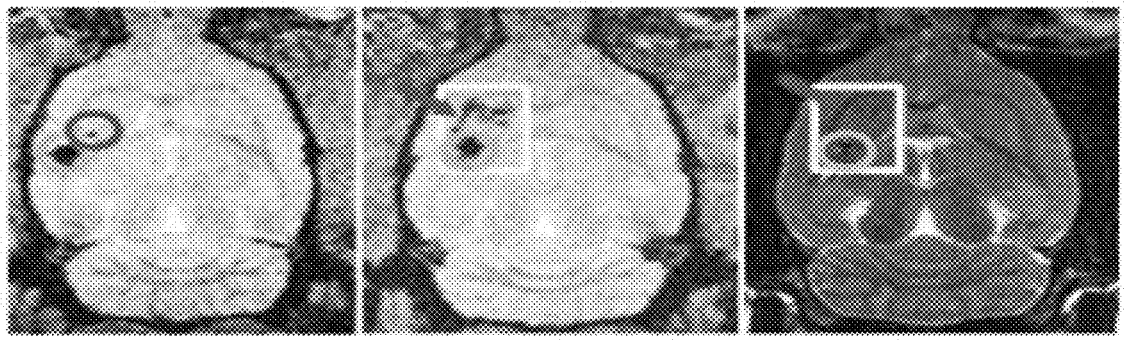
Figure 8D:
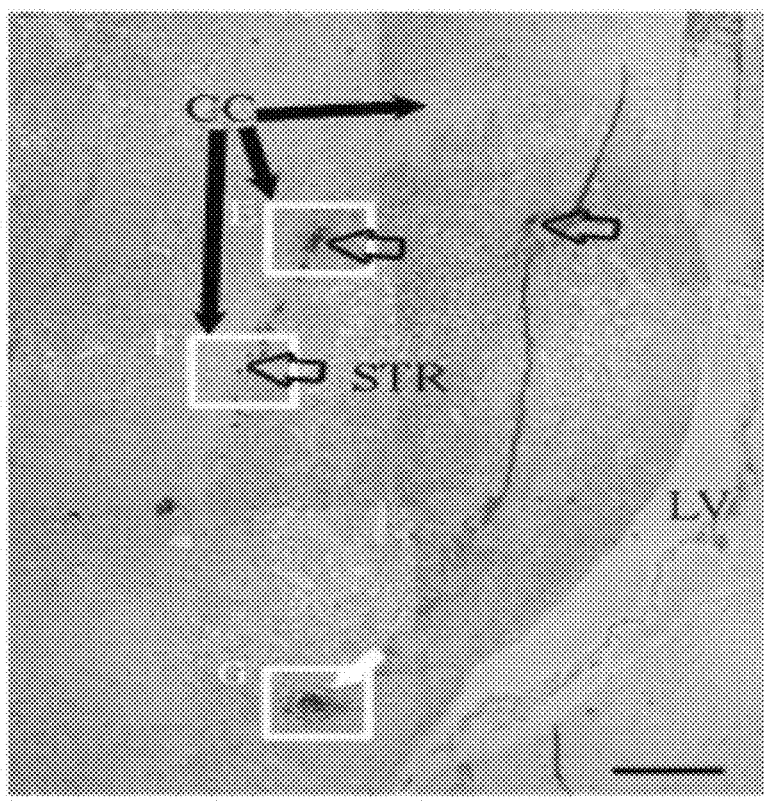
Figure 8E:
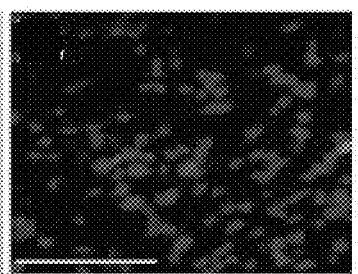
Figure 8F:
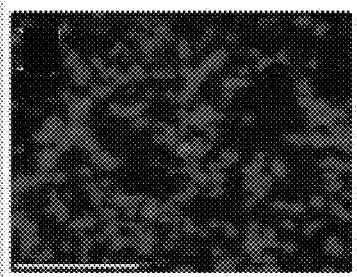
Figure 8G:
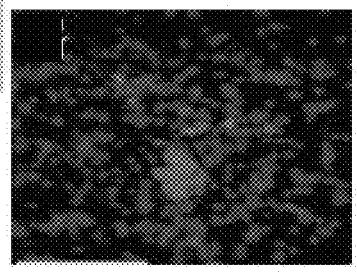

Cell tracking was done at three different time points, by applying in-vivo MRI and three different histological assessments. In-vivo MRI was conducted on selected animals treated with iron particles-labeled cells (or SPIOs only as controls, n=3 each) on day 35 post treatment. The 3D $T_2^*$ weighted images demonstrated two distinct hypointense regions for the PBS treated group: the PBS/SPIO injection site and the 6-OHDA injection sites (FIG. 8A). The latter probably resulted from bleeding in the site of 6-OHDA injection. No other hypointensities could be seen in the area between the two injections. In contrast, the 3D $T_2^*$ weighted images of the cell-treated group demonstrated a migration pathway from the site of NTF-SC injection to the striatum (FIG. 8B-8C). The 2D $T_2$ weighted image is shown in FIG. 8G for anatomical reference. Histological staining with Prussian blue for the iron particles was in excellent agreement with hypointensities in the MR images (FIG. 8D).

Further histological studies aimed at the search for human nuclear antigen. Four randomly selected animals treated with the higher dose of human NTF-SC were sacrificed for histological studies at the first time point, i.e., 7 days after they were treated with 6-OHDA. The brains of the animals were serially sectioned as described. Using the NSA methods, a large cluster of cells around the injection site were observed in each of these animals. In three out of the four specimens, cells were found to be present along 620-1920 µm from the site of transplantation in adjacent sections, indicating the beginning of cellular migration. In order to quantify the survival rate of the cells, all the cells with normal morphology were manually counted, (i.e. those that were smooth-looking and not comprising egmented nuclei with a positive dye. This measurement revealed that only 0.34±0.1% of the cells survived one week post transplantation.

On the last day of the experiment, i.e. 50 days post-treatment, NSA methods were used on 4 randomly selected animals from the PBS control group, the high MSC-treated group and the NTF-SC-treated group. This examination revealed almost no cells. In fact, around the transplantation site, only remnants of cells and signs of old bleeding were found. After sectioning other brains into 8 µm sections and using a more sensitive fluorescent based stain, a small minority of the transplanted human cells after 50 days were observed. The staining was conducted on axial sections adjacent to those in which a positive Prussian blue dye was found, and all cells positive for human nuclear antigen were demonstrated along the migration path. However, using the fluorescence method, the present inventors could not find cells along the entire migration pathway indicated by the Prussian blue stain, indicating that iron deposits did not necessarily indicate living cells by the last day of the experiment (FIGS. 8E-8G). CD68 staining for the identification of macrophages in the route of the cells was negative (data not shown). In summary, migration of human cells within the lesioned rat striatum was noted by in-vivo MRI and by histological analysis; a small minority of the cells was found to survive for at least 50 days.

CONCLUSIONS

In this report, a robust induction protocol of adult human bone marrow derived MSC into NTF-SC is described. Such cells produce and release several NTFs including BDNF and GDNF. These cells conditioned media rescued 6-OHDA-treated neuroblastoma cells. In cyclosporinized rats with unilateral striatal 6-OHDA lesions, ipsilateral transplantation of human NTF-SC was beneficial and partially attenuated amphetamine-induced rotations and other abnormal behavior, striatal dopamine levels reduction, as well as the loss of TH-immunoreactive nerve terminal network. It was also found that the NTF-SC migrated along the corpus callosum around the striatal 6-OHDA lesion into the anterior striatum, instead of migrating directly to the lesion area.

It was found that the NTF-SC secrete significantly higher levels of NTFs compared to untreated MSCs. This protocol increased the levels of BDNF and GDNF 2.3- and 5.8-fold, respectively, as compared to control human MSC. Immunocytochemical studies revealed that the induction process is robust, since almost all cells are positive for the tested NTF.

Cell-based delivery of NTFs may be potentially superior to direct infusion of NTFs since it does not require instruments of transplantation such as permanent catheters, rather than a single surgical procedure. The presently proposed medium-based induction may also be superior to viral vector delivery for achieving genetic over-expression since it circumvents safety problems. Moreover, the present inventors used xeno-free media for both the production of the MSC culture and for their induction procedure until transplantation, rendering the present method more practical and acceptable for clinical use. The platelet-based growth medium did not alter the basic mesenchymal characteristics of the MSC in terms of CD markers and mesenchymal lineage differentiation.

Human neuroblastoma cells exposed to 6-OHDA are used as an in-vitro model for PD, due to similar cellular processes that occur in the degenerating dopaminergic neurons, such as oxidative stress and apoptosis. The conditioned media of MSC and NTF-SC protected the neuroblastoma cell line from a 6-OHDA induced cell death. Although both MSC and NTF-SC demonstrated beneficial effects, NTF-SC-based treatment was more potent in protection from the 6-OHDA, specifically in higher insult concentrations. The conditioned media used in this experiment consisted of a serum-free media placed on the cells 24 hours post-induction. Therefore, it consisted of only the factors secreted by the cells, and not induction media. This strongly implies that the mechanism underlying the observed protection is the presence of secreted NTFs.

In order to perform in-vivo testing for the assumption that NTF-SC-based treatment is beneficial in a PD animal model, the present inventors first calibrated the well-established 6-OHDA-induced hemiparkinsonian rat model by injecting the specific dose of 6-OHDA into two striatal locations. As opposed to injections into the medial forebrain bundle, the present inventors used a relatively mild and progressive model of PD, probably representing an early phase of PD in human subjects. The cellular transplantation treatment was given on the day of 6-OHDA injection, therefore aiming at neuroprotection, rather than at regeneration of already-lost dopaminergic terminals. The animals were examined by two well documented behavioral tests: amphetamine-induced rotations and spontaneous motor activity in an open field.

The effect of NTF-SC treatment in terms of amphetamine-induced rotations was comparable to that found by some researches who utilized dopamine producing cells in the same animal model. The present finding that NTF-SC transplantation reduces the amphetamine-induced rotations by 40% as compared to the control group indicates that the present therapeutic strategy, of employing stem cells as inducers of neuroprotection, is efficient and comparable to dopaminergic cell replacement strategies. The NTF-SC treated group also demonstrated a positive trend in the open field test, whereas the MSC did not alter the hypoactive behavior compared to the PBS treated group.

Following the 6-OHDA lesion, the striatal TH immunoreactive fiber area of the MSC treated group was larger than in the PBS-treated animals. However, only the NTF-SC treated group demonstrated a statistically significant lesser destruction of DA nerve terminals attested by a markedly larger TH-positive area compared to the PBS treated group. As stated, only the most anterior part of the striatum benefited from the NTF-SC treatment, at a distance from the transplantation site. It is interesting to note that in that area of the striatum, the damage was not as severe as in the posterior section. Hence, NTF-SC may prove more beneficial in a moderately injured tissue, but not in a state of complete or near-complete loss of dopaminergic nerve terminals. The migratory path of the transplanted cells was observed through the corpus callosum to the anterior parts of the striatum and not directly from the transplantation site into the lesion. This might be an indication that the surviving cells affected the anterior, rather than the posterior striatum.

Although MSC partially rescued dopamine levels, only the NTF-SC-treated group demonstrated a statistically significant lesser decreases of striatal dopamine levels which makes this treatment superior to the conventional non-induced MSC-based therapy.

An important issue in stem cell research is the survival of the transplanted cells in-vivo. In this work the present inventors employed different methods over several time points in order to address this subject. Using in-vivo MRI the present inventors were able to demonstrate the migration capacity of other cells, which was highly correlated to Fe histological staining. A migratory route was observed that bypassed the lesion site along the corpus callosum and led into the anterior striatum. Such cellular migration proves two major points: firstly, that the migrated cells survived in the CNS; and secondly, that the cells moved towards a specific signal traveling along a specific route.

In an attempt to quantify the number of surviving cells, a stereological method at 7 and 50 days post treatment was used. When applying this relatively insensitive but reproducible method, it was found that the vast majority of the transplanted cells were rejected within a week post transplantation, and that no cells were found in the treated striatum after 50 days, even though immunosuppressive therapy was given. This low surviving rate is probably due to immune rejection, and to some extent immediate cellular death due to shear forces when passing though a thin syringe into the tissue. When a more sensitive method was used, with a higher signal to noise ratio, the surviving cells were highlighted, as the tissue was sliced into thin 8 μm sections and a fluorescent dye was used. Moreover, the survival of the cells in the specific location in which they were found was supported by its high correlation to the MR images and the Prussian blue stain for iron particles in the specific specimens in which we used SPIOs labeled cells. The absence of macrophages (CD68 expressing cells) along the migration route is additional evidence of the survival of the migrating transplanted cells. It is therefore implied that although only a minority of the cells survived throughout the experiment, they were sufficient to induce the described beneficial effect in the lesioned striatum. Another strong possibility is that the transplanted cells exerted their full beneficial efficiency soon after their placement into striatum and that there was no further need for their entire presence later on.

Example 3

Human Mesenchymal Stem Cells Differentiated into Neurotrophic Factors Secreting Cells Perform Glutamate Uptake The present study was performed in order to ascertain whether induction of adult hMSC into NTF-SC increases their ability to perform glutamate uptake and further to ascertain whether this uptake was significantly reduced by glutamate uptake inhibitors.

Materials and Methods

In-vitro differentiation: Donor MSCs were grown and differentiated as detailed in Example 1 herein above.

Glutamate uptake: Glutamate uptake was assessed using [$^3$H] D-aspartate (Amersham Pharmacia Biotech, Roosendaal, Netherlands), a transportable analogue of L-glutamate, which does not interact with glutamate receptors and is not metabolized. Differentiated and non-differentiated MSC were plated on poly-L-lysine coated 24 well plates, at a concentration of $2.5 \times 10^4$ cells per well. Plated cells were maintained in serum free medium (DMEM supplemented with SPN and L-Glutamine as specified for platelets medium above.) for 24 hours. Cells were rinsed twice with 0.5 ml Krebs buffer (25 mM HEPES pH 7.4, 4.8 mM KCl, 1.2 mM $KH_2PO_4$, 1.3 mM $CaCl_2$, 1.2 mM MgSO4, 6 mM glucose and 140 mM NaCl) preheated to 37° C. Cells were incubated in 0.5 ml of preheated Krebs buffer and [$^3$H] D-aspartate at a final concentration of 50 nM. Uptake was stopped after 20 minutes by three rinses with cold $Na^+$ free Krebs buffer (25 mM HEPES pH 7.4, 4.8 mM KCl, 1.2 mM $KH_2PO_4$, 1.3 mM $CaCl_2$, 1.2 mM $MgSO_4$, 6 mM glucose and 120 mM choline chloride- NaCl was replaced with choline chloride at the same osmolarity). Cells were lysed with 0.5 ml of 1 M NaOH. The radioactivity of 350 μL was determined by liquid scintillation counting. 150 μL of lysate were removed for protein concentration tests performed using Bradford assay (Bio-Rad Laboratories Ltd.). Na+ free tests were performed in 0.5 ml Na+ free Krebs buffer preheated to 37° C. Glutamate uptake inhibition was performed using 0.314 μM L-trans-Pyrrolidine-2,4-dicarboxylic acid (t-PDC, Sigma-Aldrich St. Louis), it was add after the second rinse and was incubated for 15 minutes prior to [$^3$H] D-aspartate addition. Competitive inhibition was achieved using cold (non-radioactively labeled) D-methyl-aspartate at a final concentration of 50 nM on top of the labeled [$^3$H] D-aspartate.

Results

Functional glutamate transport in cultured MSC and NTF-SC was evaluated by measuring the amount of [$^3$H] D-aspartate taken up by the cells. [$^3$H] D-aspartate is a transportable glutamate analogue that does not interact with glutamate receptors and is not metabolized. Thus, this assay provides a strong indication of the cells ability to perform glutamate uptake.

NTF-SC perform considerable [$^3$H] D-aspartate uptake as shown in FIG. 9. [$^3$H] D-aspartate uptake was significantly increased when MSC were induced into NTF-SC ($P<0.0001$). When the assay was performed in a $Na^+$ free buffer, uptake was reduced by 57.5%. Furthermore, competitive inhibition by D-methyl-aspartate reduced uptake by 86.76%, while inhibition by t-PDC a non-specific glutamate uptake inhibitor reduced glutamate uptake by over 90%.

These results suggest that induction of MSC into NTF-SC increases glutamate uptake, that NTF-SC perform significant glutamate uptake and that this uptake involves both $Na^+$ dependent and independent transport.

CONCLUSIONS

This study indicates the ability of bone marrow derived stem cells to take up glutamate. This ability is drastically improved after induction of hMSC into NTF-SC. Glutamate is extremely ubiquitous in the human CNS, however overexposure to glutamate is highly toxic. Glutamate neurotoxicity has long been known to contribute to the pathogenesis of neurological disorders such as cerebral ischemia, AD, PD, HD, epilepsy and ALS.

Transplantation NTF-SC cells near the insult sight could allow neuronal protection from glutamate toxicity by regulating extracellular glutamate levels without interfering with proper glutamate neuronal transmission. Glutamate release inhibitors and receptor antagonists are already being used to treat several neurological conditions. Riluzole, a drug used in the treatment of ALS and obsessive compulsive disorder (OCD) reduces glutamate release. Glutamate antagonists are being tested in stroke in the hope of limiting the size and severity of the ischemic insult and are already employed in several antiepileptic drugs. Specific Glutamate receptor antagonists are currently undergoing clinical tests in the treatment of AD. Nevertheless, this solution interferes with the natural functions of glutamate, increasing the plausibility of severe side effects, reduced by the use of NTF-SC.

The combined therapeutic effect of neurotrophic factors and glutamate uptake provides the best survival chances of degeneration prone neurons in each and every one of the different neurological disorders.

Example 4

Further Characterization of Neurotrophic-Factor-Secreting Cells (NTF-SCs)

Materials and Methods

Real-time reverse transcription polymerase chain reaction: Real-time PCR of GFAP was performed in an ABI Prism 7700 sequence detection system (Applied biosystems) using Sybr green PCR master mix (Applied biosystems). GAPDH gene served as a valid reference 'housekeeping' gene for transcription profiling.

The PCR was performed in a total volume of 20 µl containing 1 µl of cDNA, 1 µl each of the 3' and 5' primers (final concentration of 500 nmol/L each), 10 µl of Absolute™ QPCR SYBR® Green ROX Mix and 8 µl of DEPC water.

The amplification protocol was 40 cycles of 95° C. for 15 sec followed by 60° C. for 1 min each.

Immunocytochemistry: For immunochemistry analysis, cells were grown on 12 mm round poly-L-lysine coated glass coverslips. At the end of the experiment the medium was removed, cells were fixed with paraformaldehyde 4% (v/v) for 20 minutes at room temperature and permeabilized thereafter with 0.25% Triton X-100 (v/v) in 0.1 M PBS for 20 minutes. Non-specific binding was blocked by incubating the cells in a 0.1 M PBS solution containing 5% normal goat serum (NGS) and 1% bovine serum albumin (BSA) (Sigma) for 1 hour at 37° C. Subsequently, the cells were incubated in a 0.1 M PBS solution containing 0.25% Triton X-100 (v/v), 5% NGS and 1% BSA with primary antibodies i.e. rabbit anti-glial fibrillary acidic protein (GFAP) 1:100 (DAKO), mouse anti human nuclear h-Nuc 1:30 and mouse anti S100β 1:200 (Sigma-Aldrich, St. Louis, Mo., USA). Secondary antibodies were added for 1 hour and subsequently streptavidine-Alexa-488 conjugated goat anti-rabbit IgG antibody 1:200 (Molecular Probes, Eugene, Oreg., USA). For other staining, Alexa-488 conjugated goat anti-rabbit IgG antibody 1:200 and Rodamine-Rx-conjugated 1:200 (Jackson ImmunoResearch Laboratories, West Grove, Pa., USA) were diluted in 0.1 M PBS solution containing 0.25% Triton X-100 (v/v), 5% NGS and 1% BSA and were applied for 1 hour at room temperature. Nuclei were stained for 5 minutes with the nuclear dye DAPI 1:200 (Sigma, Aldrich). Following three rinses in PBS, the preparations were mounted in Antifaiding (Sigma, Israel) and examined using a fluorescent microscope coupled to a CCD camera (T.I.L.L. photonics, Martinsried, Germany). Excitation wavelengths (488, 405 and 568 nm for Alexa 488, DAPI and Alexa 568, respectively) were generated using a Xenon lamp coupled to a monochromator (T.I.L.L. photonics, Martinsried, Germany). Digital images were acquired using appropriate filters and combined using the TILLvisION software.

Results

The results are illustrated in FIGS. 10A-10C,

Specifically, FIGS. 10A-10C show the increase in GFAP in the differentiated cells of the present invention, wherein more than 90% of the cells express GFAP (FIG. 10C). FIGS. 11A-11C show that more than 90% of the differentiated cells of the present invention express S100.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a disease selected from the group consisting of Parkinson's, amyotrophic lateral sclerosis (ALS), Alzheimer's disease, stroke and Huntington's disease comprising administering into the CNS of a subject in need thereof a therapeutically effective amount of a population of non-genetically modified human cells, wherein said population of non-genetically modified human cells have been differentiated ex vivo from mesenchymal stem cells, wherein said population of non-genetically modified human cells express at least one mesenchymal stem cell marker and secrete both brain-derived neurotrophic factor (BDNF) and glial derived neurotrophic factor (GDNF), wherein said population of non-genetically modified human cells do not secrete nerve growth factor (NGF), wherein said at least one mesenchymal stem cell marker is selected from the group consisting of CD73, CD90 and CD105, thereby treating the disease selected from the group consisting of Parkinson's, amyotrophic lateral sclerosis (ALS), Alzheimer's disease, stroke and Huntingdon's disease.

2. The method of claim 1, wherein said non-genetically modified human cells are autologous to said subject.

3. The method of claim 1, wherein said non-genetically modified human cells are non-autologous to said subject.

4. The method of claim 1, wherein said non-genetically modified human cells are allogeneic to said subject.

5. The method of claim 1, wherein said administering to the subject comprises administering to the spinal cord of the subject.

\* \* \* \* \*

UNITED STATES PATENT AND TRADEMARK OFFICE
CERTIFICATE OF CORRECTION

PATENT NO. : 11,185,572 B2
APPLICATION NO. : 16/047129
DATED : November 30, 2021
INVENTOR(S) : Avinoam Kadouri et al.

Page 1 of 1

It is certified that error appears in the above-identified patent and that said Letters Patent is hereby corrected as shown below:

On the Title Page

Item (73) Assignee, Line 2:
"BrainStorm Ceil Therapeutics Ltd."
Should be changed to:
-- BrainStorm Cell Therapeutics Ltd. --

Signed and Sealed this
Twenty-seventh Day of December, 2022

Katherine Kelly Vidal
*Director of the United States Patent and Trademark Office*